(12) United States Patent
Kakuda

(10) Patent No.: US 9,123,235 B2
(45) Date of Patent: *Sep. 1, 2015

(54) CONTROL APPARATUS AND METHOD, RECORDING MEDIUM AND PROGRAM

(71) Applicant: Sony Corporation, Tokyo (JP)

(72) Inventor: Hiroshi Kakuda, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/075,318

(22) Filed: Nov. 8, 2013

(65) Prior Publication Data

US 2014/0062677 A1    Mar. 6, 2014

Related U.S. Application Data

(63) Continuation of application No. 13/479,535, filed on May 24, 2012, now Pat. No. 8,611,718, which is a continuation of application No. 10/509,480, filed as application No. PCT/JP03/16312 on Dec. 19, 2003, now Pat. No. 8,204,356.

(30) Foreign Application Priority Data

Jan. 30, 2003    (JP) ................................ P2003-021972

(51) Int. Cl.
*H04N 5/765*    (2006.01)
*G08C 17/02*    (2006.01)
(Continued)

(52) U.S. Cl.
CPC ................ *G08C 17/02* (2013.01); *A61K 35/76* (2013.01); *A61K 38/00* (2013.01); *A61K 39/145* (2013.01); *A61K 49/0004* (2013.01); *C07K 14/005* (2013.01); *G08C 19/28* (2013.01)

(58) Field of Classification Search
None
See application file for complete search history.

(56) References Cited

U.S. PATENT DOCUMENTS 5,589,947 A    12/1996  Sato et al.
2001/0049322 A1    12/2001  Watanabe et al.
(Continued)

FOREIGN PATENT DOCUMENTS

EP    1 443 766    8/2004
JP    06-319177    11/1994
(Continued)

OTHER PUBLICATIONS

Supplementary European Search Report under Article 153(7) EPC, mailed by European Patent Office on Oct. 22, 2009 in corresponding European Application No. EP 03 78 2821 (3 pages).

(Continued)

*Primary Examiner* — William C Vaughn, Jr.
*Assistant Examiner* — Daniel Tekle
(74) *Attorney, Agent, or Firm* — Hazuki International, LLC

(57) ABSTRACT

The present invention relates to a control apparatus and a method, a recording medium and a program, which enable to control at least one first device more efficiently and quickly through the use of a second device. The control apparatus stores at least one first operation panel information corresponding to the at least one first device received from the second device; detects the at least one first device; determines whether the at least one first operation panel information remains stored in the control apparatus; displays at least one first operation panel based on the at least one first operation panel information if the at least one first operation panel information remains stored in the control apparatus; and controls the at least one first device.

24 Claims, 33 Drawing Sheets

(51) Int. Cl.
*A61K 39/145* (2006.01)
*A61K 38/00* (2006.01)
*A61K 49/00* (2006.01)
*A61K 35/76* (2015.01)
*C07K 14/005* (2006.01)
*G08C 19/28* (2006.01)

(56) References Cited

U.S. PATENT DOCUMENTS

2002/0059617 A1\* 5/2002 Terakado et al. ............... 725/80
2004/0117831 A1 6/2004 Ellis et al.

FOREIGN PATENT DOCUMENTS

| JP | 10-271573 | 10/1998 |
| JP | 2000-196654 | 7/2000 |
| JP | 2002-016990 | 1/2002 |
| KR | 2001-0035398 | 5/2001 |
| WO | WO 99/10801 | 3/1999 |

OTHER PUBLICATIONS

Notice of Allowance dated Feb. 16, 2012, for U.S. Appl. No. 10/509,480.
Notice of Allowance dated Aug. 12, 2013, for U.S. Appl. No. 13/479,535.

\* cited by examiner

F I G. 2
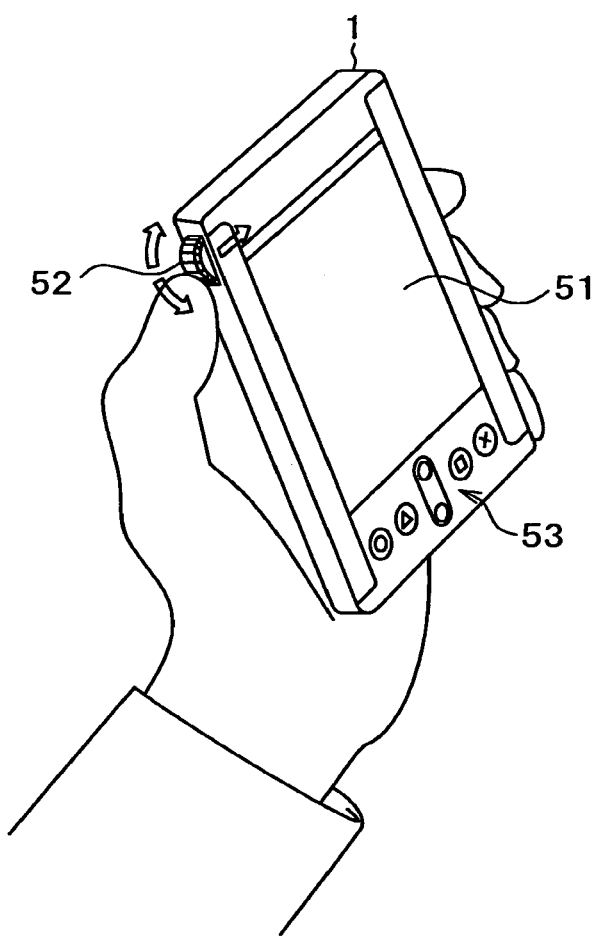

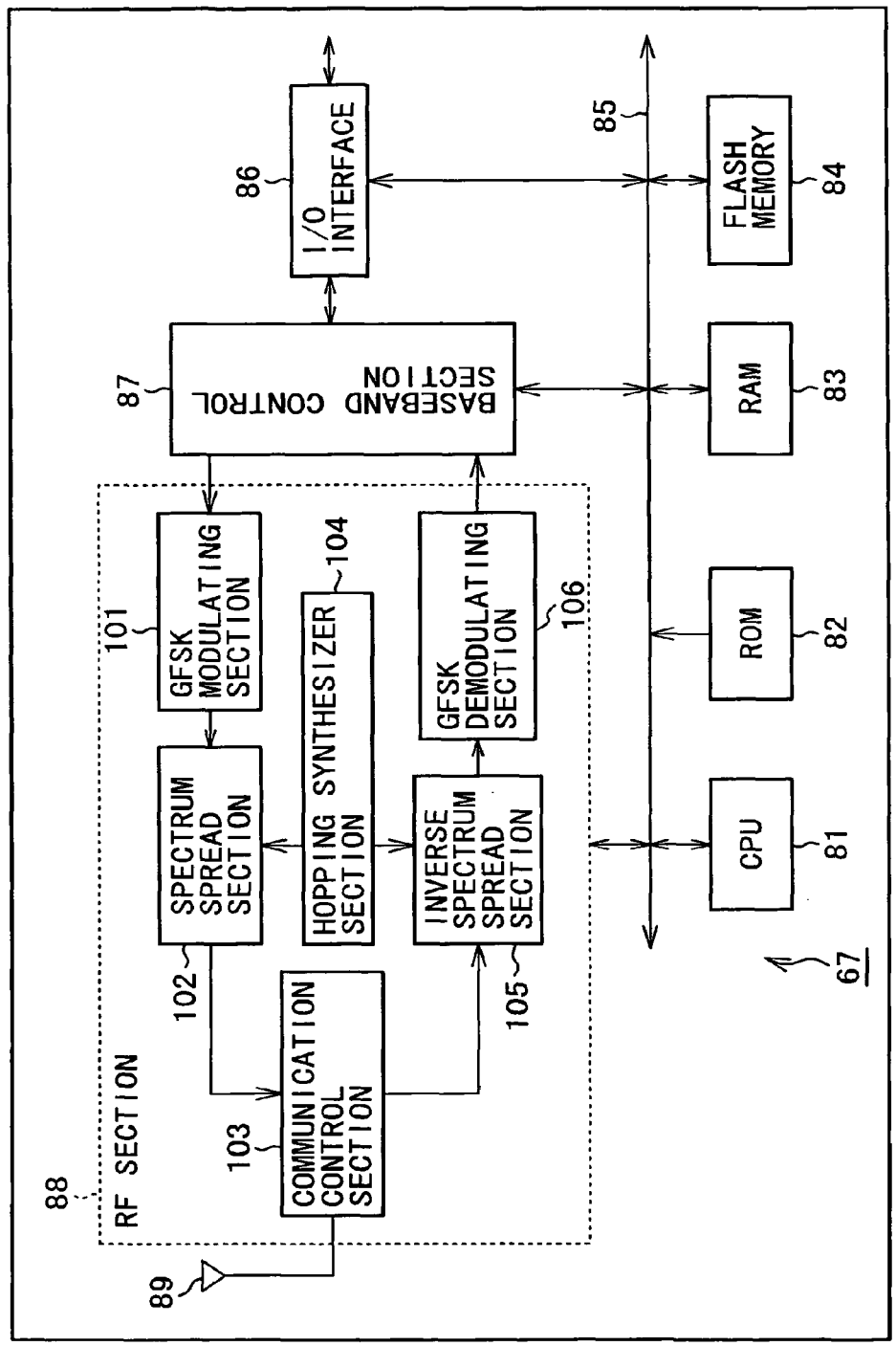
F I G. 4

F I G. 5
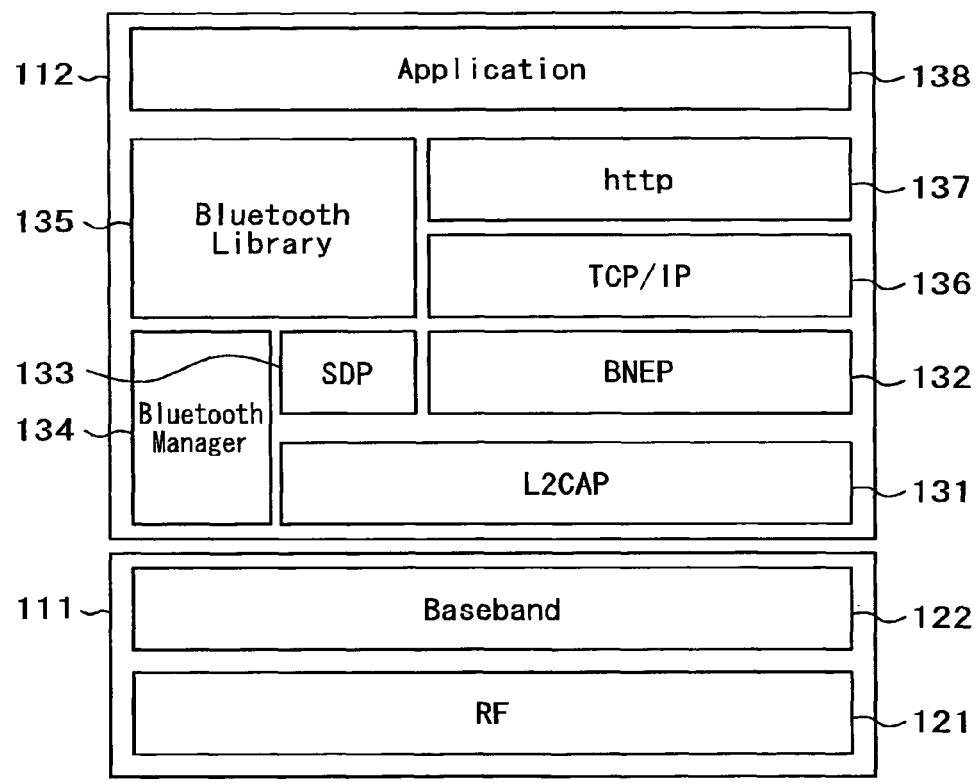

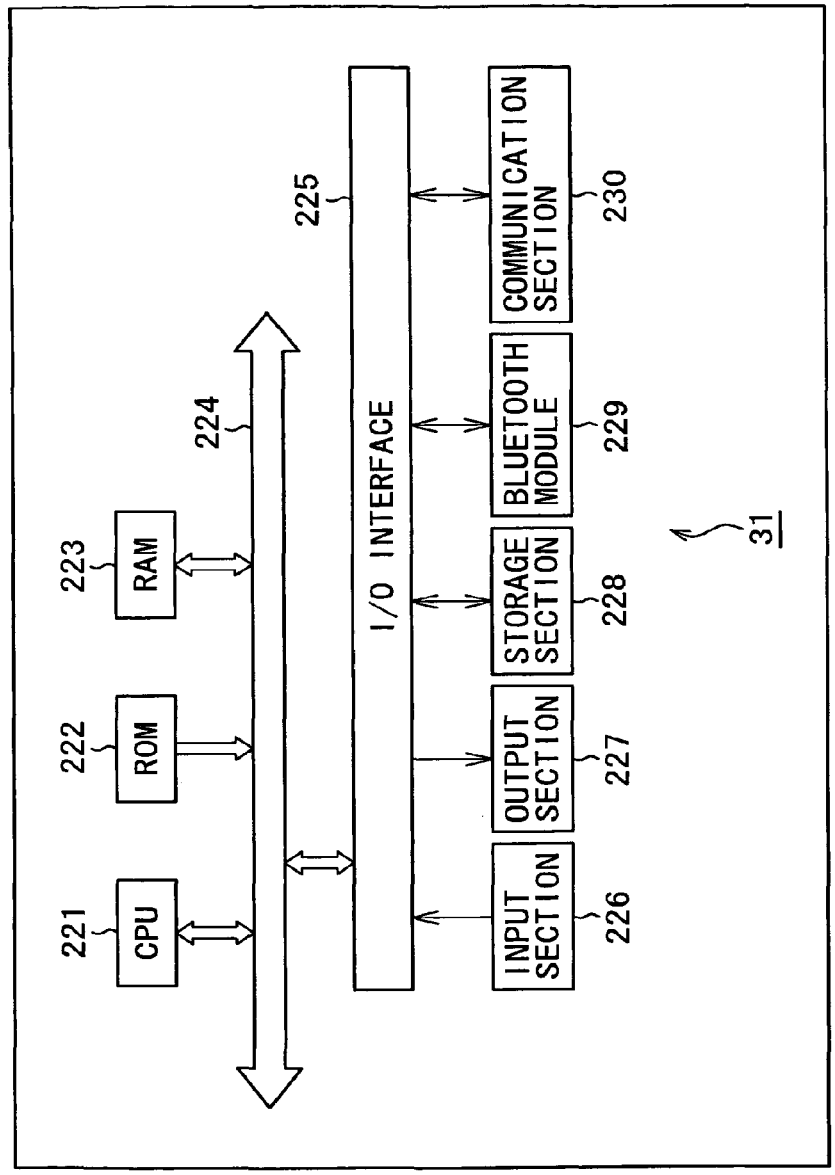

F I G. 1 1
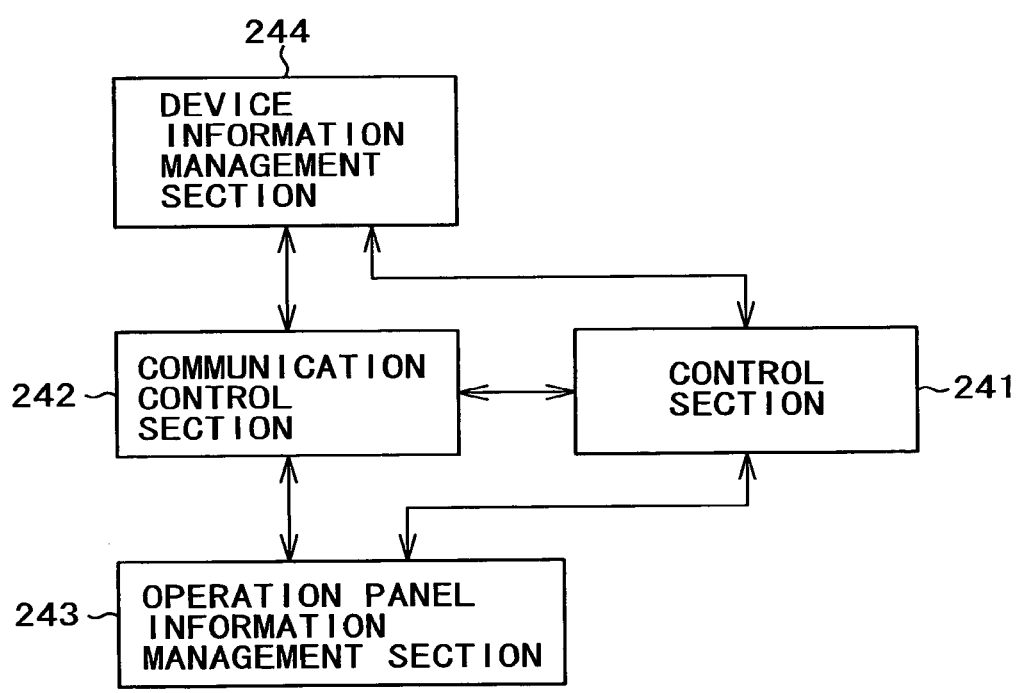

F I G. 1 3
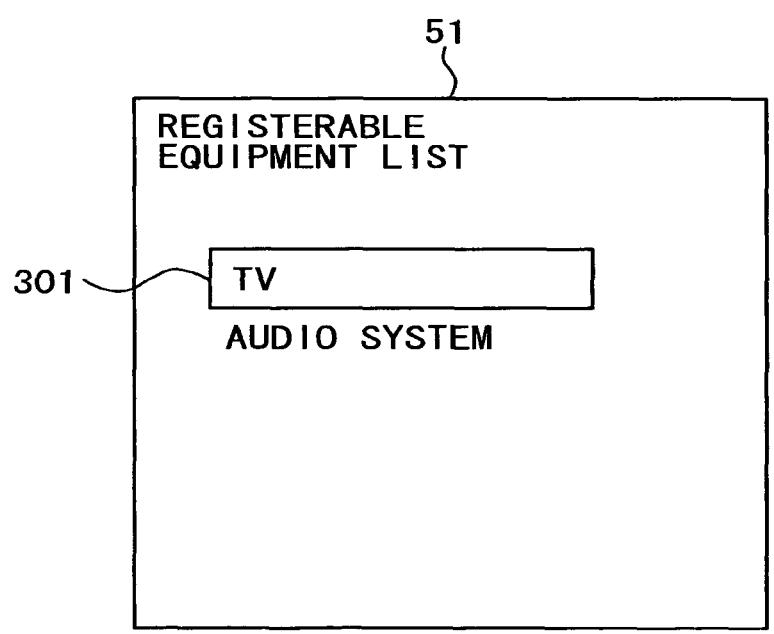

F I G. 14

| | NAME | CATEGORY | MANUFACUTURER CODE | DEVICE ID | BLUETOOTH ADDRESS |
|---|---|---|---|---|---|
| DEVICE 1 | TELEVISION | TV | 00x1 | 1234 | 08:00:46:21:94:A3 |

F I G. 18
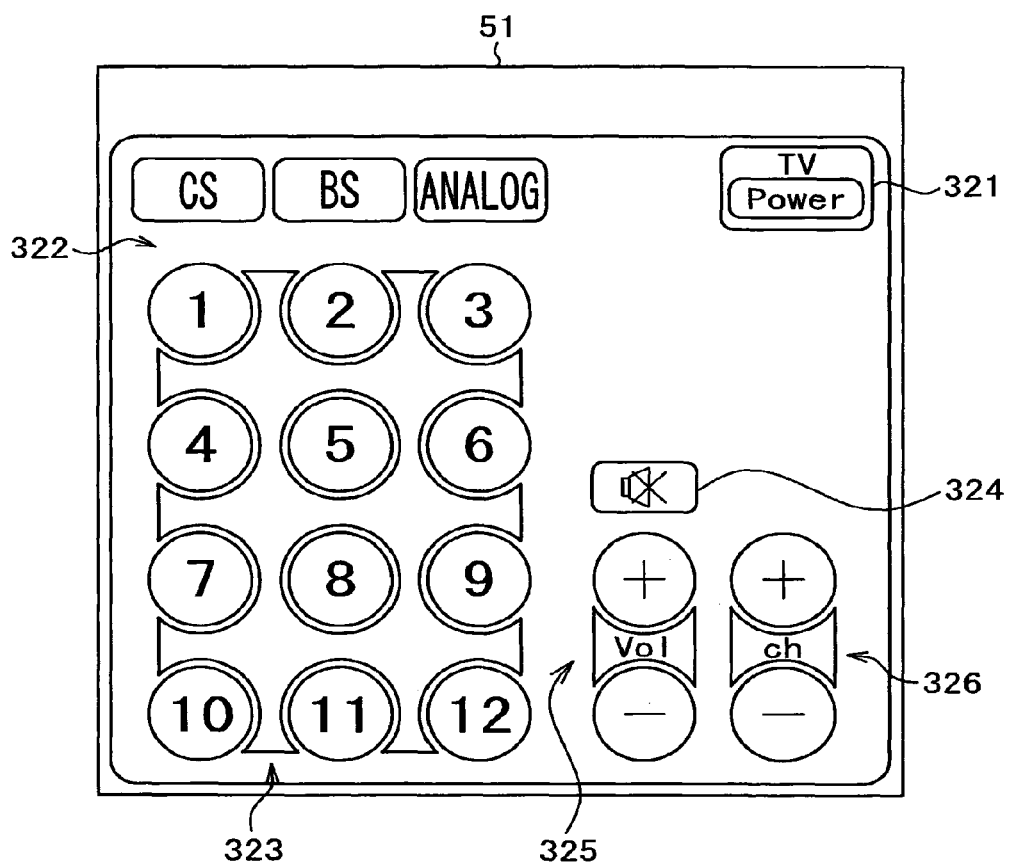

F I G. 24

|  | NAME | CATEGORY | MANUFACTURER CODE | DEVICE ID | BLUETOOTH ADDRESS |
|---|---|---|---|---|---|
| DEVICE 1 | PERSONAL COMPUTER | PC | 00x1 | 1122 | 06:00:25:63:75:B5 |
| DEVICE 2 | TELEVISION | TV | 00x1 | 1234 | 08:00:46:21:94:A3 |
| DEVICE 3 | PERSONAL COMPUTER | PC | 00x5 | 7788 | 07:01:22:34:56:78 |

F I G. 2 5

| DEVICE NAME | IP ADDRESS | MAC ADDRESS | PARENT |
|---|---|---|---|
| TELEVISION RECEIVER 21 | 192.168.0.10 | 00-30-65-BA-E9-C2 | PC 351 |
| PC 351 | 192.168.0.2 | 00-30-63-CA-E8-D1 | — |
| PC 31 | 192.168.0.11 | 00-30-65-CC-E9-C5 | PC 351 |

F I G. 2 7
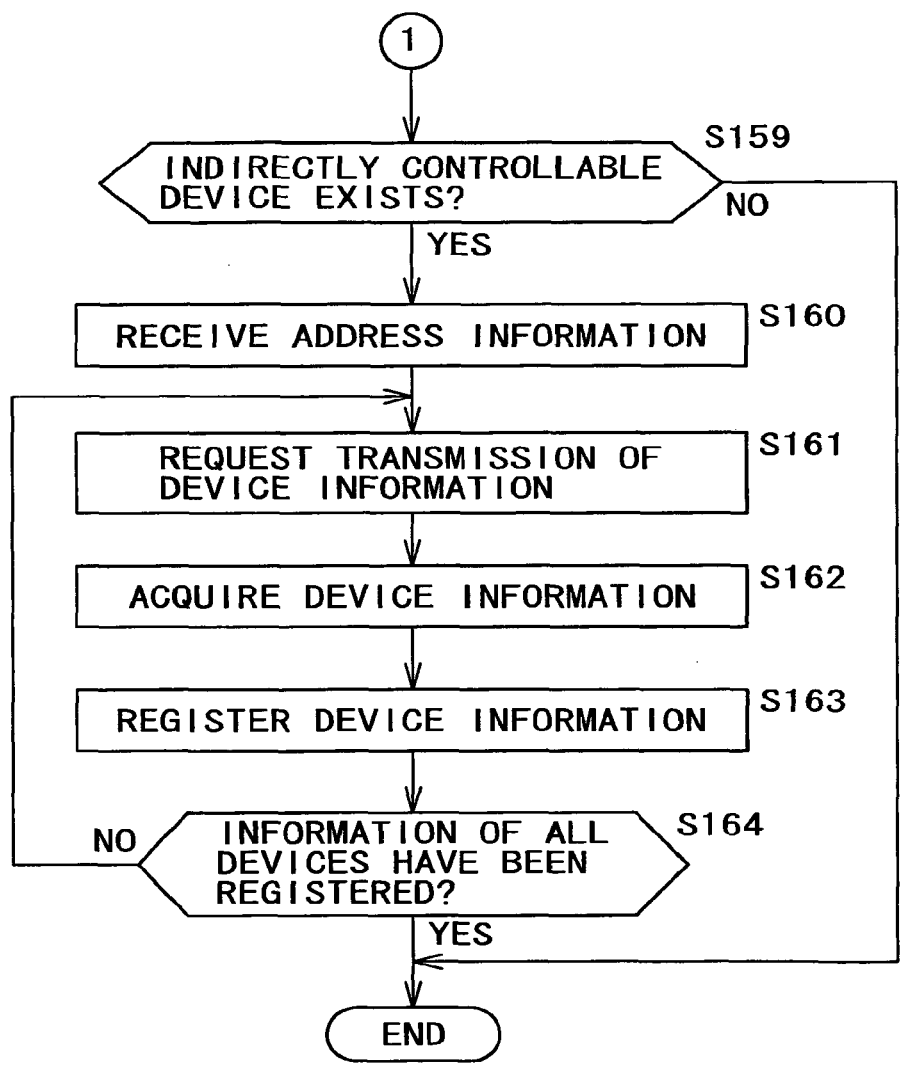

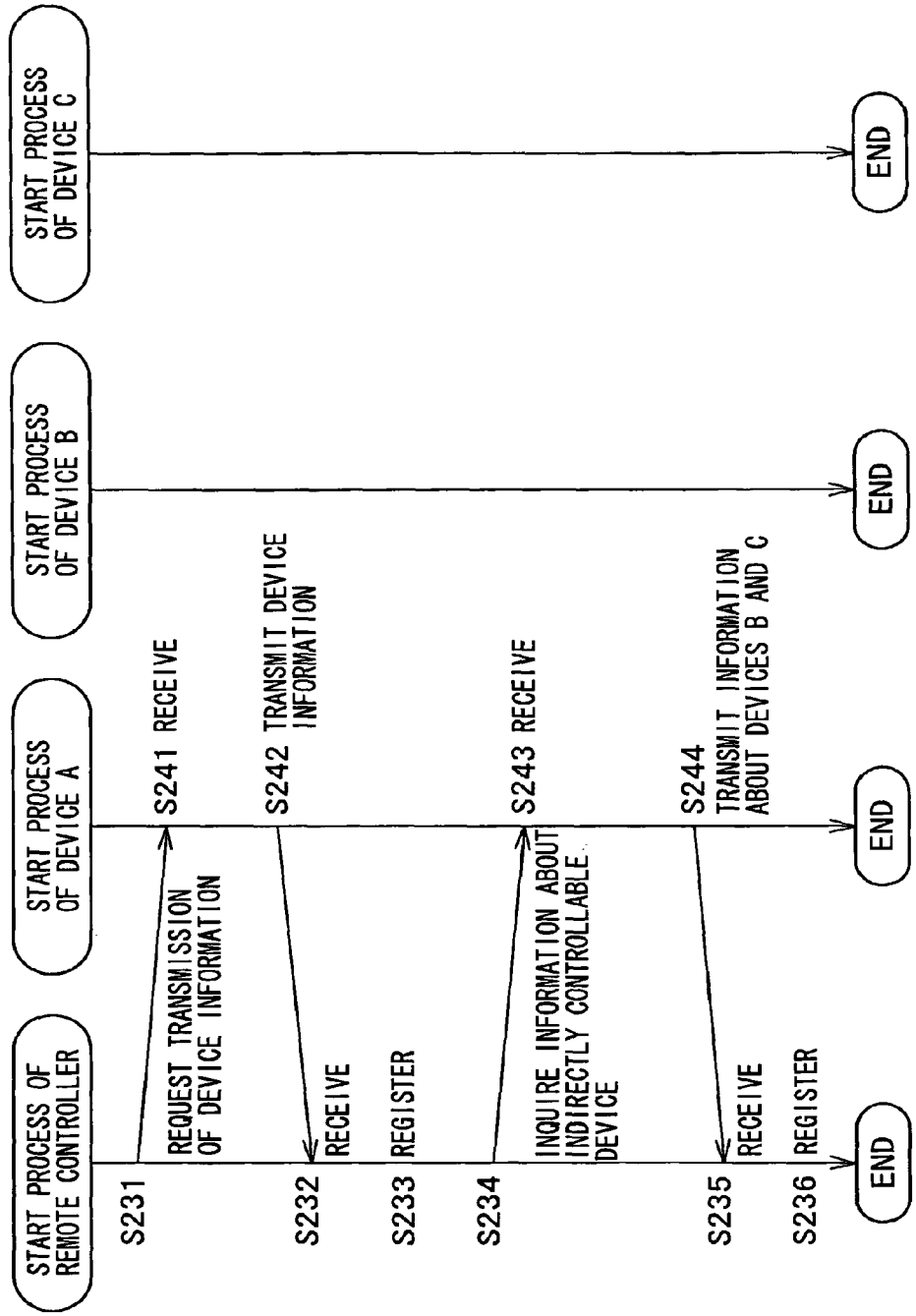

CONTROL APPARATUS AND METHOD, RECORDING MEDIUM AND PROGRAM

This application is continuation of U.S. application Ser. No. 13/479,535, filed May 24, 2012, which is a continuation of U.S. application Ser. No. 10/509,480, filed Sep. 29, 2004, now U.S. Pat. No. 8,204,356 B2, which is the U.S. National Stage Entry of PCT/JP03/16312, claiming priority to Japanese Patent Application No. JP2003-021972 filed Jan. 30, 2003, all of which are incorporated herein by reference in their entirety.

TECHNICAL FIELD

The present invention relates to a control apparatus and method, a recording medium, and a program. In particular, the present invention relates to a control apparatus and method, a recording medium, and a program, which enable to control an information processing apparatus more efficiently and quickly.

BACKGROUND ART

In the recent years, there has been widely used audio visual (AV) equipment of a new category such as hard disk recorders and digital versatile disc (DVD) recorders, and the like.

Since a remote controller normally belongs to each of these equipments, a new purchase of equipment will increase the number of remote controllers in the home. For example, the remote controller of a television receiver, a video tape recorder (VTR), or audio equipment, and others are already present in a general household.

Additionally, personal computers mounting a TV program playback function and a music playback function, or a variety of appliances such as air conditioners and lighting equipment show a tendency to increase the number of the type that is operable by a remote controller. Thus, some households may have a considerable number of remote controllers.

Therefore, a variety of techniques enabling to manage centrally so many remote controllers in an integrated manner have conventionally been proposed.

For example, Japanese Patent Application Publication No. 2002-16990 discloses the technique that enables to add the function to a remote controller by downloading display screen information of the remote controller and, based on it, displaying remote controller image.

Also, Japanese Patent Application Publication No. 6-319177 discloses the technique that enables to easily detect control target equipment if a plurality of equipment is so controllable by one remote controller.

However, the above-mentioned techniques suffer from the problem that control target equipment is limited to equipment that can communicate directly with a remote controller by infrared or the like.

In the case where besides equipment capable of communicating directly, equipment connected to that equipment can also be controlled indirectly with use of a remote controller, a user can anticipate that a variety of equipments are controllable more efficiently and quickly. This is particularly noticeable in the case where first equipment that can be controlled directly by a remote controller, and second equipment that can be controlled indirectly via the first equipment, are connected by radio or the like, and placed at different rooms.

DISCLOSURE OF THE INVENTION

The present invention has been accomplished with this circumstance in view, and is aimed at enabling control of target equipment more efficiently and quickly.

A control apparatus of the present invention is characterized by including: detection means for detecting a first information processing apparatus capable of communicating directly through wireless communication; request means for requesting, to the first information processing apparatus detected by the detection means, address information on a network of a second information processing apparatus connected via the network to the first information processing apparatus; acquisition means for acquiring operation screen information for displaying an operation screen to be operated when controlling the second information processing apparatus; display means for displaying the operation screen on the basis of the operation screen information acquired by the acquisition means; and control means, if an input is provided from the operation screen displayed by the display means, for controlling indirectly the second information processing apparatus via the first information processing apparatus on the basis of the address information sent from the first information processing apparatus in response to a request generated by the request means.

The acquisition means can acquire the operation screen information from the second information processing apparatus via the first information processing apparatus.

The acquisition means can further acquire other operation screen information for displaying other operation screen to be operated when controlling the first information processing apparatus, and the display means can display the operation screen and the other operation screen, on the basis of the operation screen information and the other operation screen information acquired by the acquisition means.

A control method of a control apparatus of the present invention is characterized by including: a detection step of detecting a first information processing apparatus capable of communicating directly through wireless communication; a request step of requesting, to the first information processing apparatus detected by the process in the detection step, address information on a network of a second information processing apparatus connected via the network to the first information processing apparatus; an acquisition step of acquiring operation screen information for displaying an operation screen to be operated when controlling the second information processing apparatus; a display step of displaying the operation screen on the basis of the operation screen information acquired by the process in the acquisition step; and a control step, if an input is provided from the operation screen displayed by the process in the display step of controlling indirectly the second information processing apparatus via the first information processing apparatus on the basis of the address information sent from the first information processing apparatus in response to a request generated by the process in the request step.

A program recorded in a recording medium of the present invention, and a program of the present invention are characterized by including: a detection step of detecting a first information processing apparatus capable of communicating directly through wireless communication; a request step of requesting, to the first information processing apparatus detected by the process in the detection step, address information on a network of a second information processing apparatus connected via the network to the first information processing apparatus; an acquisition step of acquiring operation screen information for displaying an operation screen to be operated when controlling the second information processing apparatus; a display step of displaying the operation screen on the basis of the operation screen information acquired by the process in the acquisition step; and a control step, if an input is provided from the operation screen displayed by the process in the display step of controlling indirectly the second information processing apparatus via the first information processing apparatus on the basis of the address information sent from the first information processing apparatus in response to a request generated by the process in the request step.

In the control apparatus and the method, and the program of the present invention, the first information processing apparatus capable of communicating directly through wireless communication is detected, and address information on a network of the second information processing apparatus connected to the first information processing apparatus via the network is requested to the detected first information processing apparatus. In addition, operation screen information for displaying an operation screen to be operated when controlling the second information processing apparatus is acquired, and the operation screen is displayed on the basis of the acquired operation screen information. If an input is provided from the displayed operation screen, the second information processing apparatus is controlled indirectly via the first information processing apparatus on the basis of the address information sent from the first information processing apparatus in response to a request.

BRIEF DESCRIPTION OF DRAWINGS

FIG. 2 is a perspective view showing an example of an appearance of a remote controller in FIG. 1;

FIG. 4 is a block diagram showing an example of a configuration of a Bluetooth module in FIG. 3;

FIG. 5 is a diagram showing a protocol stack of Bluetooth;

FIG. 10 is a block diagram showing an example of a configuration of a personal computer in FIG. 1;

FIG. 11 is a block diagram showing an example of a functional configuration of the personal computer in FIG. 10;

FIG. 13 is a diagram showing an example of a screen displayed in step S4 of FIG. 12;

FIG. 14 is a diagram showing an example of information registered by the process of FIG. 12;

FIG. 18 is a diagram showing an example of a screen displayed in step S37 of FIG. 16;

FIG. 24 is a diagram showing an example of device information;

FIG. 25 is a diagram showing an example of address information;

FIG. 27 is a flow chart, continued from FIG. 26, for explaining the registration process of the remote controller;

FIG. 35 is a flow chart for explaining an operation of the control system in FIG. 20.

BEST MODE FOR CARRYING OUT THE INVENTION

Figure 1:
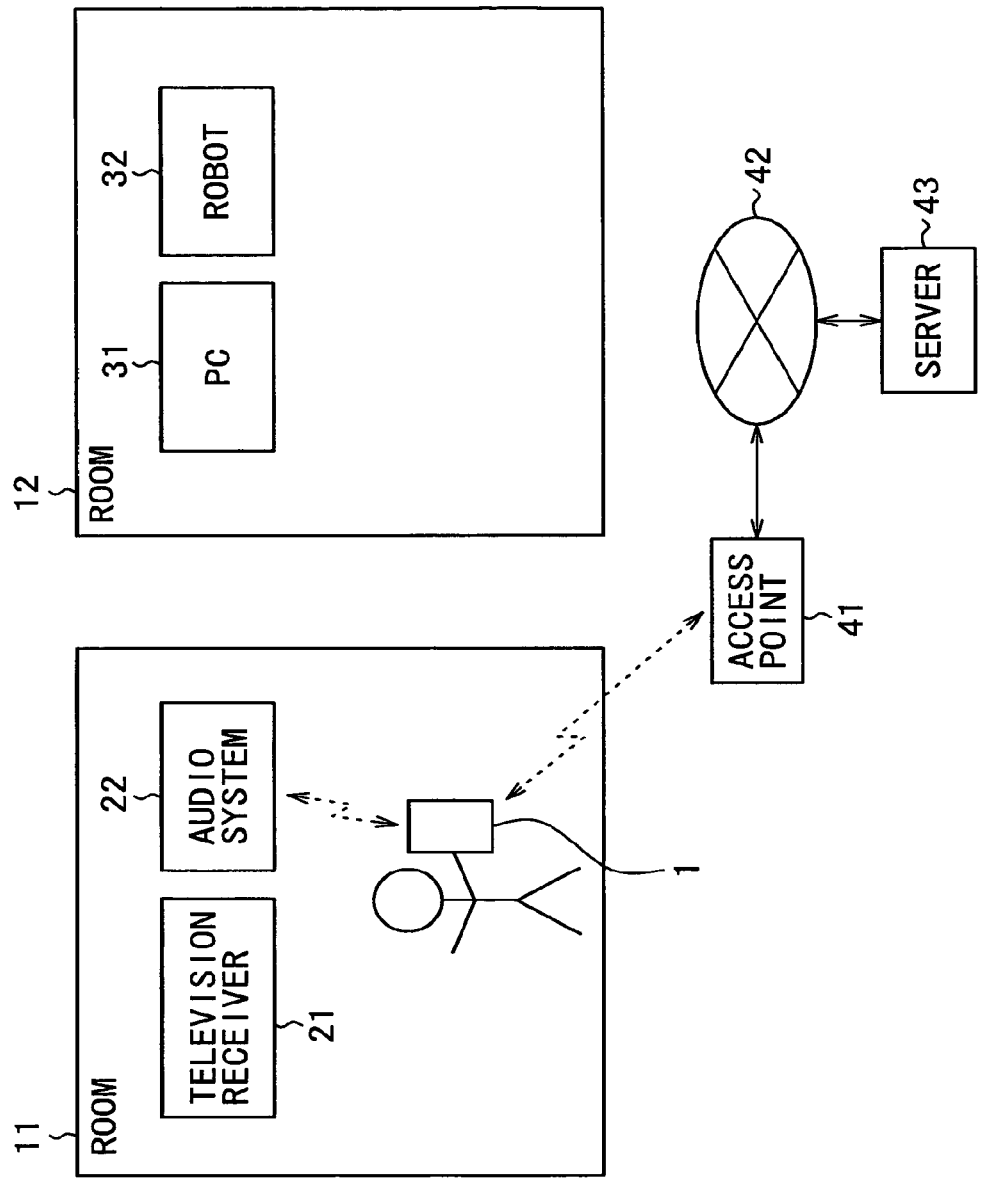
FIG. 1 is a diagram showing an example of a configuration of a control system to which the present invention is applied.

FIG. 1 is a diagram showing an example of a configuration of a control system to which the present invention is applied.

A remote controller (a control apparatus) 1 has the function of wireless communication facility in conformity with, for example, Bluetooth communication, Institute of Electrical and Electronics Engineers (IEEE) 802.11a, 802.11b, 802.11g, and the like. By such wireless communication, the remote controller 1 sends a command based on an input from a user, to a device (an information processing apparatus) as a control object, thereby controlling the device.

In other words, the device to be controlled by the remote controller is also provided with a communication facility by Bluetooth communication and a communication facility such as IEEE802.11b.

In the example of FIG. 1, as a device to be controlled by the remote controller 1, a television receiver 21 and an audio system 22 are placed at a room 11. A personal computer (PC) 31 and a robot 32 are placed or present at a room 12.

Upon detecting that a user picks up the remote controller 1 because, for example, vibration having a predetermined threshold value or more occurred in a built-in vibration sensor, the remote controller 1 makes search for control target devices to detect a device existing in the vicinity. The term "vicinity" here denotes a range of such as several tens centimeters to several meters, in which it is capable of detecting a device placed in the room where the remote controller 1 is present at that time. Alternatively, there may be configured such that a user may set a range in which the remote controller 1 makes search for devices (the range of the vicinity).

Upon detecting a control target device by search, the remote controller 1 communicates with the device by, for example, a hyper text transfer protocol (HTTP), and obtains panel information from the device operation for displaying an operation panel (a screen on which a variety of buttons are arranged), which is operated by a user when controlling the device. Devices to be controlled by the remote controller 1 store respectively the operation panel information described in a hyper text markup language (HTML) and, in response to a request from the remote controller 1, provide the operation panel information to the remote controller 1 by wireless communication such as Bluetooth.

That is, a system between a client and a server is to be implemented by the remote controller 1 and the device, and the operation panel information is provided from the device as the server, to the remote controller 1.

For example, upon detecting that a user picks up the remote controller 1 at the room 11 of FIG. 1, the remote controller 1 detects by search the television receiver 21 and the audio system 22, as a controllable device. The remote controller 1 also obtains, from the television receiver 21 and the audio system 22, the respective operation panel information by Bluetooth communication, and displays operation panels on the basis of the obtained information.

Therefore, an operation panel for operating the television receiver 21 and an operation panel for operating the audio system 22 are displayed on a liquid crystal display (LCD) 51 (FIG. 2), which is formed on the surface of the remote controller 1. If a plurality of devices is so detected, the editing of operation panel information (the splitting of frames of an HTML file) is performed in the remote controller 1, in order to display the operation panels of the plurality of devices on a single LCD 51.

A touch panel is superposed in the LCD 51. When a user operates a predetermined button on the operation panel, a command corresponding to that operation is sent to the device. In the example of FIG. 1, an arrow in a broken line indicates that a predetermined control command is sent from the remote controller 1 to the audio system 22.

For example, because a user goes out of the room 11 along with the remote controller 1, it is out of the communication coverage with devices (the television receiver 21 and the audio system 22), the operation panels that were displayed until then are cleared.

Likewise at the room 12, at predetermined timing, for example, upon detecting that a user picks up the remote controller 1, the remote controller 1 makes search for devices. In this case, based on information obtained from the personal computer 31 and the robot 32, an operation panel to be operated when controlling the personal computer 31, and an operation panel to be operated when controlling the robot 32 are displayed on the LCD 51 in the remote controller 1.

Therefore, if only the user enters the communication coverage with the devices while carrying the remote controller 1, an operation panel corresponding to the device in the vicinity can be displayed, without performing by himself/herself any operation to the remote controller 1.

In the example of FIG. 1, there is provided an access point 41, which is wirelessly communicatable with the remote controller 1 by Bluetooth communication, IEEE802.11b, and the like. For example, if the operation panel information is not stored in the detected device, or if a function is added to the device and it is therefore necessary to obtain new operation panel information in order to utilize the function, the remote controller 1 communicates with the access point 41 and accesses to a server 43 via a network 42, in order to download the operation panel information from the server 43.

This enables to cope with the addition of functions to the device, thereby causing the remote controller 1 to display an operation panel that is optimal to the function of the device at that time.

FIG. 2 is a perspective view showing an example of the appearance of the remote controller 1.

A casing of the remote controller 1 is made of such size as to be able to grip and operate by one hand, as shown in FIG. 2. The LCD 51, on which operation panels of various devices are displayed, is formed in the front face of the casing of the remote controller 1. In the LCD 51, the touch panel is superposed so as to detect a position (a button), which a user pressed by the tip of a finger, or the like.

Further, a jog dial 52 is disposed at an upper portion on the side face of the casing of the remote controller 1. When selecting a button or an icon displayed on the LCD 51, the jog dial 52 is operated to roll, or operated to press in the direction of the inward of the main body, as indicated by outline arrows in the figure. For example, in the case where a plurality of operation panels are vertically arranged in a contiguous manner, the user can scroll the display range of the LCD 51 to select an operation panel by operating to roll the jog dial 52.

Figure 3:
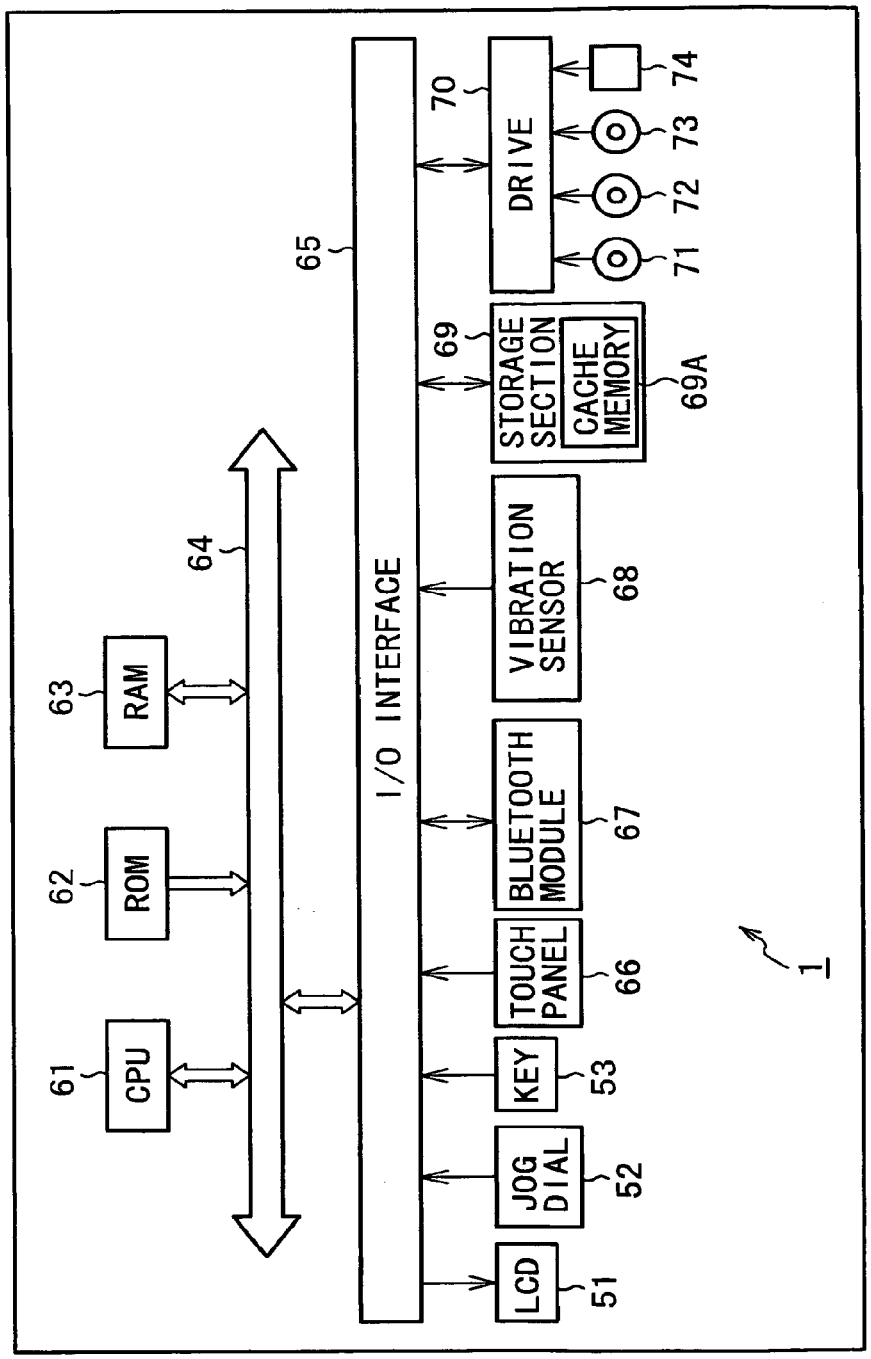
FIG. 3 is a block diagram showing an example of an internal configuration of the remote controller in FIG. 2.

The user operates a key 53 when inputting various instructions to a central process unit (CPU) 61 (see FIG. 3). For example, a search start button to be operated when starting search, and a display switching button to be operated when switching the display if a plurality of operation panel information are obtained by the remote controller 1 may be disposed as the key 53.

FIG. 3 is a block diagram showing an example of the internal configuration of the remote controller 1.

The CPU 61 executes a variety of process under a program stored in a read only memory (ROM) 62, or a program loaded from a storage section 69 to a random access memory (RAM) 63. Data and the like necessary for the CPU 61 to execute a variety of process are stored suitably in the RAM 63.

The CPU 61, the ROM 62, and the RAM 63 are mutually connected via a bus 64. An input/output interface 65 is also connected to the bus 64.

The LCD 51, the jog dial 52, the key 53, and the touch panel 66 arranged so as to superpose on the LCD 51 are connected to the input/output interface 65. Also to the input/output interface 65, a Bluetooth module 67 as a wireless communication module is connected in order to make search or control of devices, or communicate with the access point 41.

In the example of FIG. 3, the Bluetooth module 67 performing communication in conformity with Bluetooth communication is provided as a wireless communication module for making search and control of devices. In place of the Bluetooth module 67, or together with the Bluetooth module 67, a wireless local area network (LAN), such as the above-mentioned IEEE802.11b, may be provided. Alternatively, a module performing infrared communication may be provided so as to make search and control of devices by the communication with use of infrared ray.

A vibration sensor 68 for detecting vibration generated in the casing of the remote controller 1, and the storage section 69 including a flash memory and a hard disk are also connected to the input/output interface 65. As described later, a variety of device information about devices are stored in the storage section 69, and operation panel information (an HTML file) obtained from the devices are stored in a cache memory 69A of the storage section 69.

A connector of universal serial bus (USB), for example, is formed on the surface of the remote controller 1, and a drive 70 connected to the connector via a USB cable is suitably connected to the input/output interface 65.

A magnetic disk 71, an optical disk 72, a magneto-optical disk 73, or a semiconductor memory 74 is attached to the drive 70, as required. Computer programs read out of these storage media are installed to the storage section 69. By any one of the magnetic disk 71 through the semiconductor memory 74, the operation panel information may be provided to the remote controller 1.

FIG. 4 is a block diagram showing an example of a configuration of the Bluetooth module 67 in FIG. 3.

A CPU 81 expands a control program stored in a ROM 82 to a RAM 83, and controls the overall operation of the Bluetooth module 67. The CPU 81 through the RAM 83 are mutually connected via a bus 85.

A flash memory 84 is connected to the bus 85. In the flash memory 84, there are stored, for example, Bluetooth device names, which are set to respective Bluetooth devices (equipment having a Bluetooth module) and are changeable by a user according to his/her preference, and Bluetooth addresses proper to the respective Bluetooth devices.

Based on an instruction from the CPU 81, an input/output interface 86 manages the input/output of data supplied via the input/output interface 65 of FIG. 3, and data supplied from a baseband control section 87.

The baseband control section 87 supplies data, which is for example supplied from the input/output interface 86, to a Gaussian frequency shift keying (GFSK) modulating section 101, in order to send the data to a control target device, and, when data is supplied from a GFSK demodulating section 106, outputs the data to the bus 85 or the input/output interface 86. In the baseband control section 87, there are suitably performed various control such as communication link control, packet control, logic channel control and security control, or a process such as error correction encoding, decoding, and data randomizing.

The GFSK modulating section 101 of a radio frequency (RF) section 88 limits by a filter a high radio frequency components of data supplied from the baseband control section 87, and performs frequency modulation as primary modulation, and then outputs the obtained data to a spectrum spread section 102.

The spectrum spread section 102 switches a carrier frequency on the basis of a frequency hopping pattern to be instructed from a hopping synthesizer section 104, and outputs a signal obtained after subjecting the supplied data to spectrum spread, to a communication control section 103.

A inverse spectrum spread section 105 performs hopping of the received frequency on the basis of a frequency hopping pattern to be instructed from the hopping synthesizer section 104, thereby obtaining, for example, a signal from the device. The inverse spectrum spread section 105 also performs the inverse spectrum spread of the obtained signal, and outputs the resultant signal to the GFSK demodulating section 106. The GFSK demodulating section 106 performs GFSK modulation of the signal supplied from the inverse spectrum spread section 105, and outputs the obtained data to the baseband control section 87.

With use of a 2.4 GHz band, the communication control section 103 sends through an antenna 89, for example, a signal carrying a predetermined command, which has been subjected to spectrum spread. The communication control section 103 also outputs the received signal through the antenna 89 to the inverse spectrum spread section 105.

FIG. 5 is a diagram showing an example of a protocol stack of a personal area network (PAN) profile in Bluetooth communication. For example, the device control by the remote controller 1 is performed by the PAN profile.

The protocol stack is composed of a hardware section 111 and a software section 112. A physical layer (a RF layer) 121 of the hardware section 111 is a protocol for performing wireless communication with use of a frequency band of 2.4 GHz, and performing analog conversion on data supplied from a baseband layer 122, a process inverse to it, and the like. The baseband layer (baseband layer) 122 is a protocol for providing an interface of send/receive data packets to the physical layer 121. Concretely, it performs a packet creation, encoding, or decoding, as well as a designation of send/receive frequency for managing frequency hopping, and a time base slot management.

A logical link control and adaptation protocol (L2CAP) (a logic link control layer) 131 of the software section 112 is a protocol for controlling the overall of Bluetooth system and providing an interface between an upper level layer and a lower level layer. More specifically, it performs data sorting according to the type of protocol, a conversion of packet length, and the like. A Bluetooth network encapsulation protocol (BNEP) 132 is a protocol for providing communication between the equipment of slaves connected by multipoint connections. A service discovery protocol (SDP) 133 is a protocol for detecting functions and services to be provided from other equipment. Like the baseband layer 122, a Bluetooth manager 134 is a protocol for managing communication links in Bluetooth communication, and instructs, for example, the setting of the communication link and the setting of various parameters associated with the set communication link.

A Bluetooth library 135 contains a variety of components necessary for the communication. A transmission control protocol/internet protocol (TCP/IP) layer 136 controls TCP/IP communication with the detected device. A HTTP layer 137 manages the communication with use of HTTP. An application layer 138 implements file transfer, LAN connection and the like based on Bluetooth.

Figure 6:
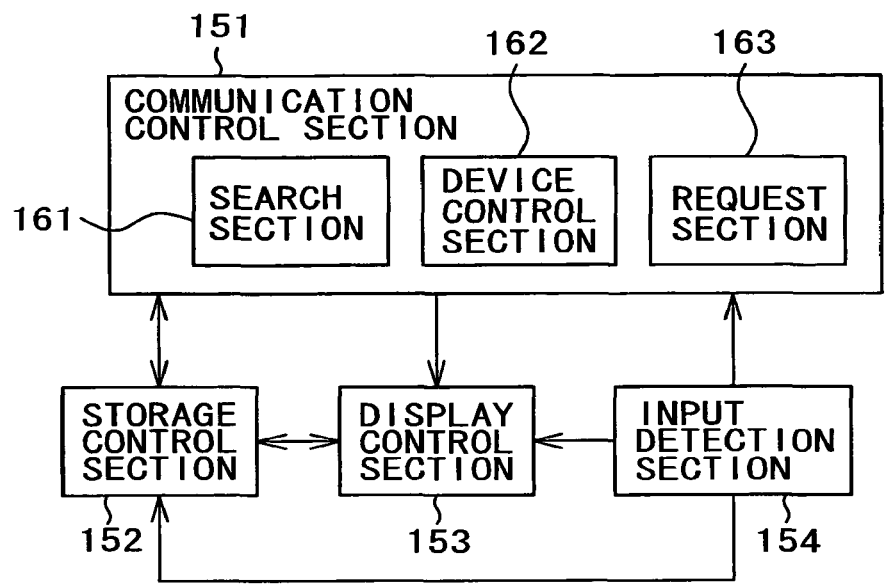
FIG. 6 is a block diagram showing an example of a functional configuration of a remote controller.

FIG. 6 is a block diagram showing an example of a functional configuration of the remote controller 1 having the foregoing configuration. Respective functional sections shown in FIG. 6 can be implemented under a predetermined control program executed by the CPU 61.

A communication control section 151 manages the operation of the Bluetooth module 67, and controls Bluetooth communication with the devices. Therefore, if in place of the Bluetooth module 67, a wireless LAN module or the like is provided, the operation thereof is to be controlled by the communication control section 151. The following description will be made mainly of the case where the remote controller 1 performs control of the devices by Bluetooth communication.

The communication control section 151 has a search section 161, a device control section 162, and a request section 163. The search section 161 searches devices are present in the vicinity by inquiry (query) and page (call) that are specified in Bluetooth, for example, in a predetermined cycle, or at predetermined timing, such as when a user picks up the casing of the remote controller 1. Information indicating the result of search by the search section 161 is outputted to a storage control section 152 and a display control section 153.

The device control section 162 sends the searched device a command corresponding to input from a user, and controls the device (e.g., a channel switch to the television receiver 21, etc.) That is, information indicating the user input detected by an input detection section 154 is outputted to the device control section 162 of the communication control section 151.

In order to control indirectly a second device connected via a network to a first device that can communicate directly with the remote controller 1, the request section 163 requests to the first device the address information on the network of the second device, as described later in detail.

The storage control section 152 manages data to be stored in the storage section 69, and provides suitably the stored data to the communication control section 151, and the like. The storage control section 152 manages, for example, information about the control target device and information an operation history of the user. As described later, in order to control devices with use of the remote controller 1, the user is required to previously register information about the devices.

The display control section 153 controls the display of the LCD 51. For example, when the communication control section 151 obtains the operation panel information from the control target device, and supplies it to the display control section 153, the display control section 153 causes the LCD 51 to display an operation panel, on the basis of the supplied information.

The input detection section 154 detects a user input to the key 53 and the touch panel 66. Information indicating the detected user input is outputted suitably to the storage control section 152, the display control section 153, and the like.

Figure 7:
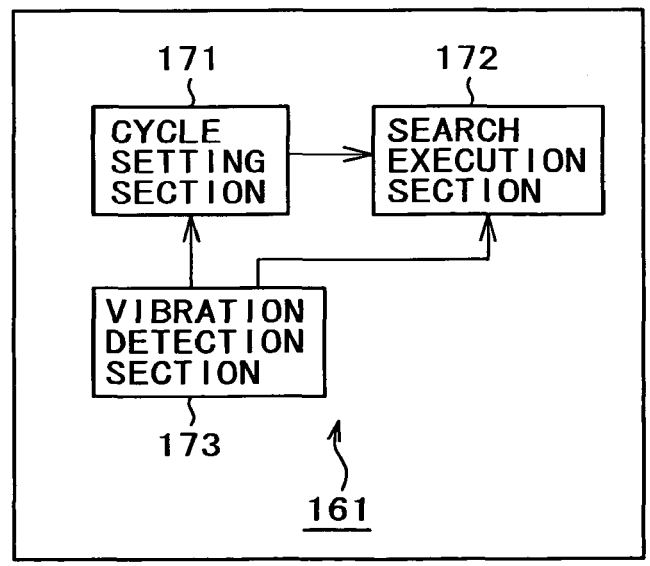
FIG. 7 is a block diagram showing an example of a configuration of a search section in FIG. 6.

FIG. 7 is a block diagram showing an example of a detailed configuration of the search section 161 in FIG. 6.

A cycle setting section 171 sets a cycle of execution of search, depending on a situation of the remote controller 1 at that time. As a default cycle of execution of search, for example, the cycle of 10 seconds is set to the remote controller 1. If any device is not detected by search, the cycle setting section 171 sets a longer cycle instead of the default cycle, as a cycle of execution of search. Information indicating the cycle set by the cycle setting section 171 is outputted to a search executing section 172.

The search executing section 172 makes search (inquiry and page) of devices, in accordance with the cycle to be set by the cycle setting section 171. In addition, the search executing section 172 makes search of devices when a vibration detection section 173 detects vibration more than a predetermined threshold value. The result of search by the search executing section 172 is outputted suitably to the storage control section 152 and the display control section 153.

The vibration detection section 173 monitors the output of the vibration sensor 68, and detects vibration generated in the remote controller 1. For example, upon detecting vibration more than a predetermined threshold value, the vibration detection section 173 recognizes that the casing of the remote controller 1 was picked up, and outputs information indicating this to the cycle setting section 171 and the search executing section 172.

Figure 8:
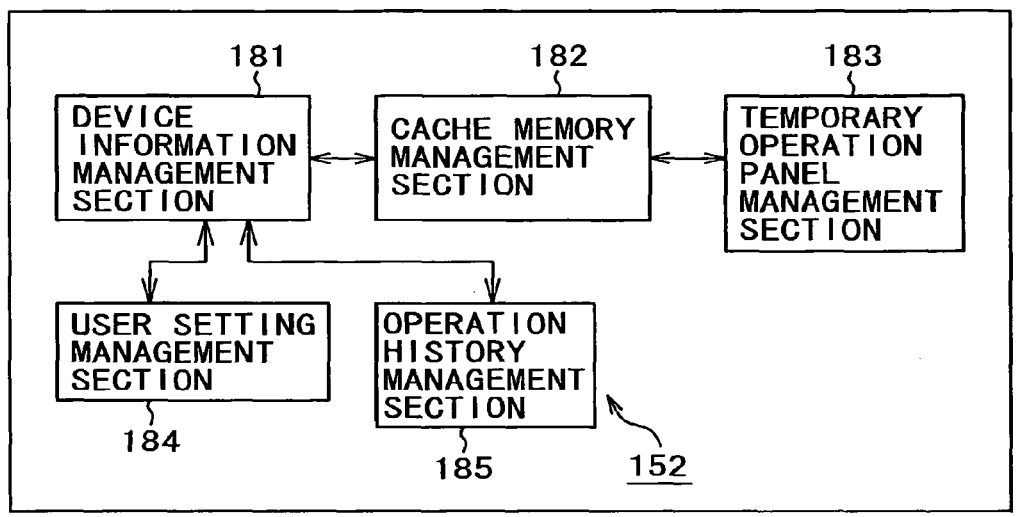
FIG. 8 is a block diagram showing an example of a configuration of a storage control section in FIG. 6.

FIG. 8 is a block diagram showing an example of a detailed configuration of the storage control section 152 in FIG. 6.

A device information management section 181 manages device information, which is registered by a registration operation by the user, and supplied from the communication control section 151. The device information to be managed by the device information management section 181 contain, for example, device names, categories (equipment type of the devices), manufacturer codes, device IDs, Bluetooth addresses and the like. The device information management section 181 provides suitably the managed information to a user setting management section 184, an operation history management section 185, and the like.

A cache memory management section 182 causes a cache memory 69A to store the operation panel information, which the communication control section 151 obtains from the devices, and manages it. As the management of the operation panel information, the cache memory management section 182 clears, for example, operation panel information having a low frequency of use, or operation panel information after elapse of predetermined time after it was stored. The cache memory management section 182 also outputs the operation panel information stored in the cache memory 69A to the display control section 153.

A temporary operation panel management section 183 manages information for displaying a temporary operation panel, and outputs it to the display control section 153, as required. As described later, until operation panel information is obtained from the device detected by search, a temporary operation panel according to the type of the device is displayed on the LCD 51 in the remote controller 1. For example, if the television receiver 21 is detected by search, a temporary operation panel for utilizing the function of general television receivers is displayed on the LCD 51, until operation panel information exclusive for the television receiver 21 is obtained from the television receiver 21. The information for displaying the temporary operation panel so displayed is also outputted to the cache memory management section 182, and then managed by the cache memory 69A.

In the storage section 69 of the remote controller 1, for example, information of the operation panel for utilizing the function of general television receivers, information of the operation panel for utilizing the function of general VTRs, information of the operation panel for utilizing the function of general digital versatile disc (DVD) players, and the like are previously prepared as temporary operation panel information.

The user setting management section 184 manages, for example, a user setting about display of the operation panel, on the basis of the information supplied from the input detection section 154. The operation history management section 185 manages an operation history such as the contents that the remote controller 1 controlled the devices, and its time, on the basis of the information supplied from the input detection section 154. The setting information managed by the user setting management section 184 and the history information managed by the operation history management section 185 are outputted suitably to the device information management section 181.

Figure 9:
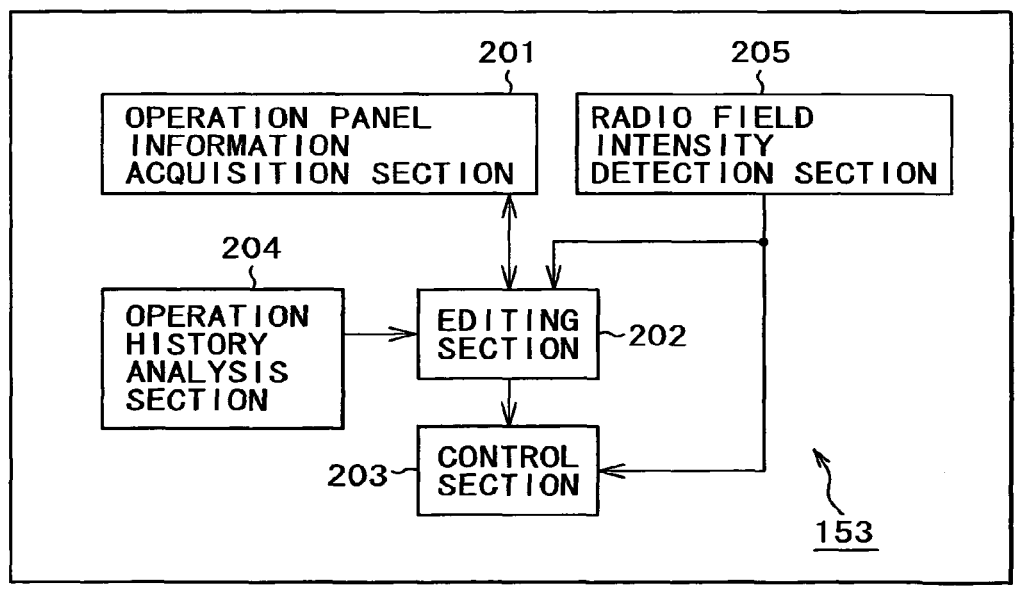
FIG. 9 is a block diagram showing an example of a configuration of a display control section in FIG. 6.

FIG. 9 is a block diagram showing an example of a detailed configuration of the display control section 153 in FIG. 6.

An operation panel information acquisition section 201 acquires the operation panel information managed by the cache memory management section 182 of the storage control section 152, or the operation panel information, which is provided from devices and then supplied from the communication control section 151, and outputs it to an editing section 202.

The editing section 202 edits the operation panel information supplied from the operation panel information acquisition section 201 in order to create new operation panel information for causing the LCD 51 to display an operation panel. For example, when operation panel information about two devices are supplied from the operation panel information acquisition section 201, the editing section 202 performs editing of the operation panel information (the splitting of frames of an HTML file), such that respective operation panels are displayed on the upper half and the lower half of the LCD 51. The operation panel information created by the editing section 202 is outputted to the control section 203.

In the editing performed by the editing section 202, as required, there is referred to information of the analysis result of the operation history to be supplied from an operation history analysis section 204.

The control section 203 controls the operation of the LCD 51 so as to display an operation panel on the LCD 51, on the basis of the operation panel information supplied from the editing section 202.

The operation history analysis section 204 analyzes the preference of the user on the basis of the operation history managed by the operation history management section 185 of the storage control section 152. For example, if a plurality of operation history information is obtained by the editing section 202, the operation history analysis section 204 analyzes the preference of the user to the respective operation panels, and outputs the analysis result to the editing section 202.

A radio field intensity detection section 205 detects an intensity of a radio wave received in the Bluetooth module 67, on the basis of the output from the communication control section 151. Information indicating the detected intensity of the radio wave is outputted to the editing section 202 and the control section 203. As to n operation panel of a device, the receivable radio of which is weak, for example, because it is apart a predetermined distance or more from the remote controller 1, the display thereof is controlled such that one having higher transparency is displayed (so as to be displayed in paler-tone).

FIG. 10 is a block diagram showing an example of a configuration of the personal computer 31 that is a device to be controlled by the remote controller 1.

Since the personal computer 31 has basically the similar configuration as that of the remote controller 1 shown in FIG. 3, the description of overlapping portions is appropriately omitted.

A Bluetooth module 229 is connected to an input/output interface 225. The Bluetooth module 229 performs the communication by Bluetooth with the Bluetooth module 67 of the remote controller 1, and for example, in response to a request from the Bluetooth module 67, sends the operation panel information stored in the storage section 228.

A communication section 230 sends and receives a variety of information with the other devices via a wired or wireless network. The communication section 230 also sends and receives information with a variety of equipment connected over the Internet.

FIG. 11 is a block diagram showing an example of a functional configuration of the personal computer 31 in FIG. 10. Respective functional sections shown in FIG. 11 are to be implemented by the execution of a predetermined control program by the CPU 221 in FIG. 10.

A control section 241 controls operations of the entire personal computer 1 (a communication control section 242, an operation panel information management section 243, and a device information management section 244). The communication control section 242 controls the Bluetooth communication in the Bluetooth module 229, or the communication in the communication section 230.

The operation panel information management section 243 manages the operation panel information stored in the storage section 228 and, in response to a request from the remote controller 1, reads out the operation panel information and provides it. The device information management section 244 manages device information containing, for example, a name, a category (personal computer), a manufacturer code, a device ID, and a Bluetooth address and the like of a personal computer 31, and provides it to the remote controller 1.

The television receiver 21, the audio system 22 and the robot 32 in FIG. 1 have the similar configuration as that of the personal computer 31 shown in FIG. 10 and FIG. 11. Therefore, as required, FIG. 10 and FIG. 11 can also be cited as the configuration of the television receiver 21, the audio system 22 and the robot 32. To the television receiver 21 and the audio system 22, some configuration inherent in individual devices, such as a tuner section and a speaker section, are added to the configuration of FIG. 10.

The operation of the control system in FIG. 1 will next be described.

Figure 12:
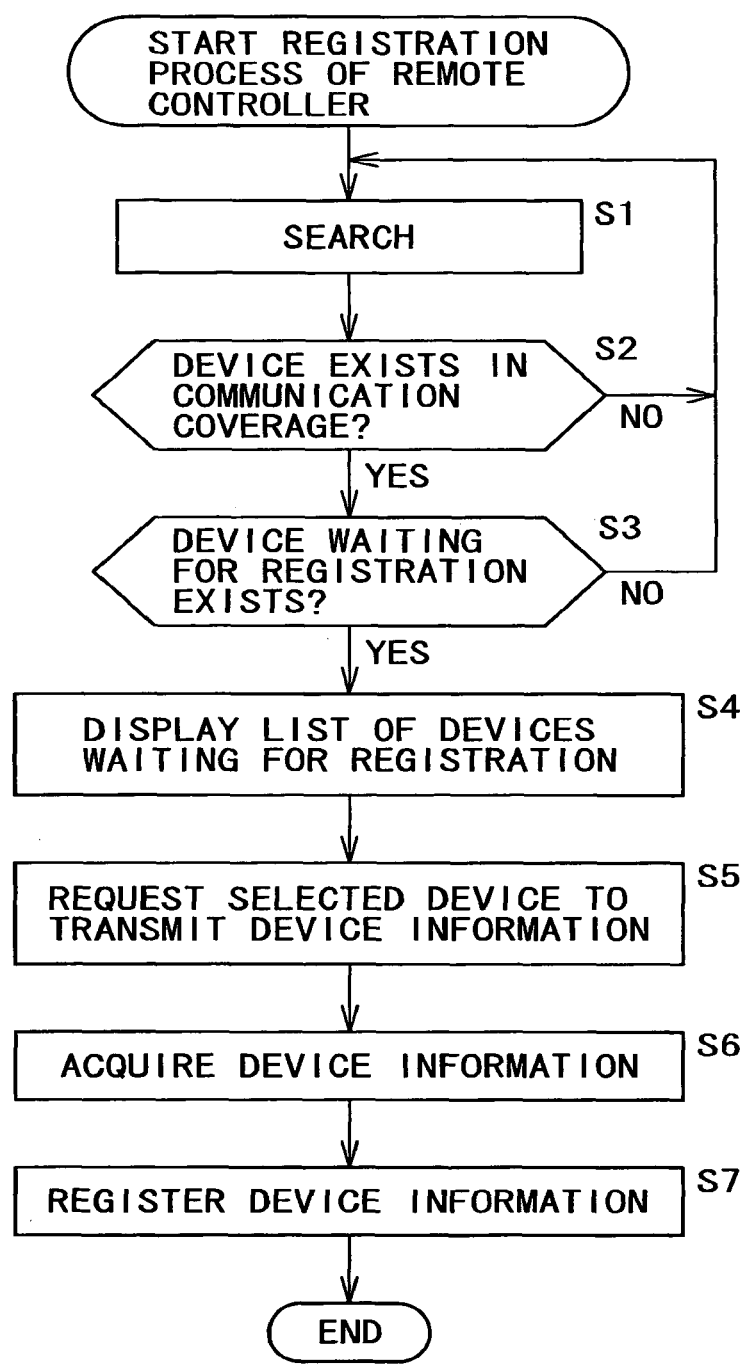
FIG. 12 is a flow chart for explaining a registration process of a remote controller.

Referring to a flow chart of FIG. 12, a process of the remote controller 1 for registering the device information is first described.

When a user instructs the registration of the device information, the search section 161 activates the Bluetooth module 67 to search (inquiry and page) the devices in step S1.

The search section 161 determines in step S2 whether or not a device is present in the communication coverage. If it is determined that no device is present, the process return to step S1 to repeat search. If a device is present in the coverage of an electromagnetic wave emitted from the Bluetooth module 67, a response to the search is made from the device.

If the search section 161 determines in step S2 that devices is present in the communication coverage, the process advances to step S3 to determine whether or not there is any device waiting for registration among the devices detected by search. For example, in order that the device is operable with use of the remote controller 1, a user, who registers the device information of the device in the remote controller 1, is required to set the status of the device to a registration wait state by a predetermined operation.

If the search section 161 determines in step S3 that there is no device waiting for registration among the detected devices, the process returns to step S1 to execute repetitively the foregoing process. Here, if no device waiting for registration is detected although the search is repetitively executed a predetermined number of times, the process is terminated.

If the search section 161 determines in step S3 that there is a device waiting for registration, the search section 161 outputs the information of the detected device to the display control section 153 (the control section 203 (FIG. 9)).

In step S4, the display control section 153 causes the LCD 51 to display a list of devices waiting for registration (devices capable of registering the device information), on the basis of output from the search section 161.

FIG. 13 is a diagram showing an example of a screen to be displayed on the LCD 51 in step S4.

In the example of FIG. 13, a message of "Registrable equipment list" is displayed on the upper part of the screen, and "TV (television receiver 21)" and "Audio system (the audio system 22)" are displayed therebelow, as a device to which the registration wait state is set. In other words, the screen of FIG. 13 is taken to be the case where a user sets the television receiver 21 and the audio system 22, which are placed in the room 11 of FIG. 1, to a registration wait state, and performs a registration operation.

Text information of the "TV" and the "Audio system" in FIG. 13 are to be displayed on the basis of the category information of devices, which was obtained by search from the television receiver 21 and the audio system 22, respectively.

If the screen shown in FIG. 13 is displayed, for example, by pressing directly a surface of the LCD 51, a user moves a cursor 301 to select a device that the user registers. The user's input is detected by the input detection section 154, and notified to the communication control section 151 (the device control section 162).

In step S5, the device control section 162 requests a device, which a user instructed to register its device information, to send the device information. In response to the request from the remote controller 1, the device information previously stored is read out in the device, and the read device information is provided to the remote controller 1 by Bluetooth communication.

In step S6, the device control section 162 controls the Bluetooth module 67 to obtain the device information sent from the device. The obtained device information is outputted from the device control section 162 to the storage control section 152 (the device information management section 181).

In step S7, the device information management section 181 causes the storage section 69 to store the supplied device information, and registers it.

FIG. 14 is a diagram showing an example of device information to be managed by the device information management section 181.

As show in FIG. 14, for example, a device name, a device category, a manufacturer code, a device ID, and a Bluetooth address are registered as the device information.

FIG. 14 indicates the case where the television receiver 21 was selected on the selection screen of FIG. 13, and "Television" in the name, "TV" in the category, "00x1" in the manufacturer code, "1234" in the device ID, and "08:00:46:21:94:A3" in the Bluetooth address are registered relative to a Device 1 (the television receiver 21).

The foregoing process is executed repetitively to add sequentially the information of the respective devices to the table shown in FIG. 14. Since the device control section 162 creates a command in response to information of such as the registered manufacturer code, it is thereafter possible that the remote controller 1 operates a device, the device information of which was registered.

Referring to a flow chart of FIG. 15, a process to be executed by the device in response to the process of FIG. 12 will next be described. The following is the case where process is executed by the television receiver 21.

In step S21, based on the user input to the input section 226 (FIG. 10), the control section 241 of the television receiver 21 determines whether or not setting to the registration wait state is instructed, and waits until it determines that the setting is instructed.

If the control section 241 determines in step S21 that the setting to the registration wait state is instructed, for example, because a predetermined button is operated, the process advances to step S22 to set the status of the television receiver 21 to the registration wait state.

By this means, the Bluetooth module 229 repetitively executes inquiry scan and page scan. Upon receipt of a radio wave from the remote controller 1, the remote controller 1 is informed that it is set to the registration wait state.

In step S23, the communication control section 242 determines whether or not the remote controller 1 requests transmission of the device information, and waits until it determines that the transmission is requested.

If the communication control section 242 determines in step S23 that the remote controller 1 requests the transmission of the device information, the process advances to step S24 to send the device information managed by the device information management section 244. That is, by the device information management section 244, the device information stored in the storage section 228 is read out and then sent from the communication control section 242 to the remote controller 1.

As described above, on receipt of the device information sent from the device, the remote controller 1 registers it (step S7 in FIG. 12).

Referring to a flow chart of FIG. 16, a process of the remote controller 1 to display the operation panel will next be described. This process is executed when the control target device is detected by the search process performed in a predetermined cycle.

When the search section 161 informs that the device is detected, in step 31, the device information management section 181 of the storage control section 152 refers to the information managed in the storage section 69, and determines whether or not the device information of the detected device is already registered.

If the device information management section 181 determines in step S31 that the device information of the detected device is not registered, the process advances to step S32 to perform the registration process, which has been described by referred to FIG. 12. In other words, when a device waiting for registration is detected, transmission of the device information is requested of the detected device, and the device information sent from the device in response to the request is registered.

After the device information is registered, the process in step S33 is skipped, and the succeeding process is executed.

On the other hand, if the device information management section 181 determines in step S31 that the device information of the detected device, such as the device ID, the Bluetooth address, and the like are already registered in the storage section 69, the process advances to step S33. For example, in the case where the information as shown in FIG. 14 is already registered and the television receiver 21 is detected by search, it is determined that the device information is registered.

In step S33, the cache memory management section 182 determines whether or not the operation panel information of the detected device is remained in the cache memory 69A. If determined that it is not remained, the process advances to step S34.

If the operation panel information is not remained in the cache memory 69A, information indicating this is outputted from the cache memory management section 182 to the temporary operation panel management section 183. The temporary operation panel management section 183 outputs the display control section 153 the information displaying a temporary operation panel (hereinafter, referred to as temporary operation panel information), depending on the category of the detected device.

The temporary operation panel information outputted from the temporary operation panel management section 183 is acquired by the operation panel information acquisition section 201 of the display control section 153, and then outputted via the editing section 202 to the control section 203.

In step S34, the control section 203 causes the LCD 51 to display a temporary operation panel on the basis of the supplied information.

Figure 17:
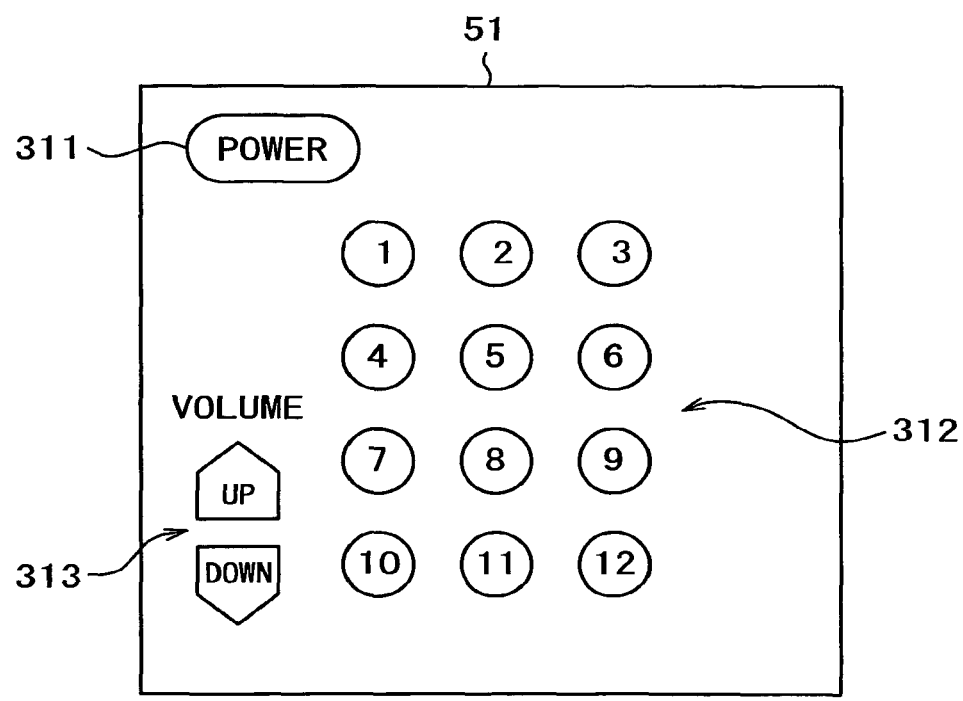
FIG. 17 is a diagram showing an example of a screen displayed in step S34 of FIG. 16.

FIG. 17 is a diagram showing an example of the temporary operation panel to be displayed on the LCD 51 in step S34.

For example, in the case where the television receiver 21 is detected and the operation panel information of the television receiver 21 is not remained in the cache memory 69A, such an operation panel as shown in FIG. 17, which is intended for operating the function set to a general television receiver by the remote controller 1, is displayed on the LCD 51, irrespective of manufacturer and the like.

In the example of FIG. 17, a power button 311 to be operated when switching an on/off of a power supply is displayed on the upper left of the temporary operation panel of the television receiver 21, and a numeric keypad 312 to be operated when switching channels is displayed on the lower right. In addition, a volume button 313 to be operated when adjusting the volume is displayed on the lower left of the temporary operation panel. The power button 311, the numeric keypad 312, and the volume button 313 are prepared in common for remote controllers of general television receivers, irrespective of manufacturer and function.

Such a temporary operation panel is displayed until the operation panel information for displaying an operation panel exclusive for the television receiver 21 is sent from the detected television receiver 21. Therefore, a user can operate the television receiver 21 by utilizing the temporary operation panel, until operation panel information is sent from the television receiver 21 and an operation panel (the operation panel exclusive for the television receiver 21) is displayed on the basis of the information. In other words, the user can operate the television receiver 21 immediately after the television receiver 21 is detected.

Figure 16:
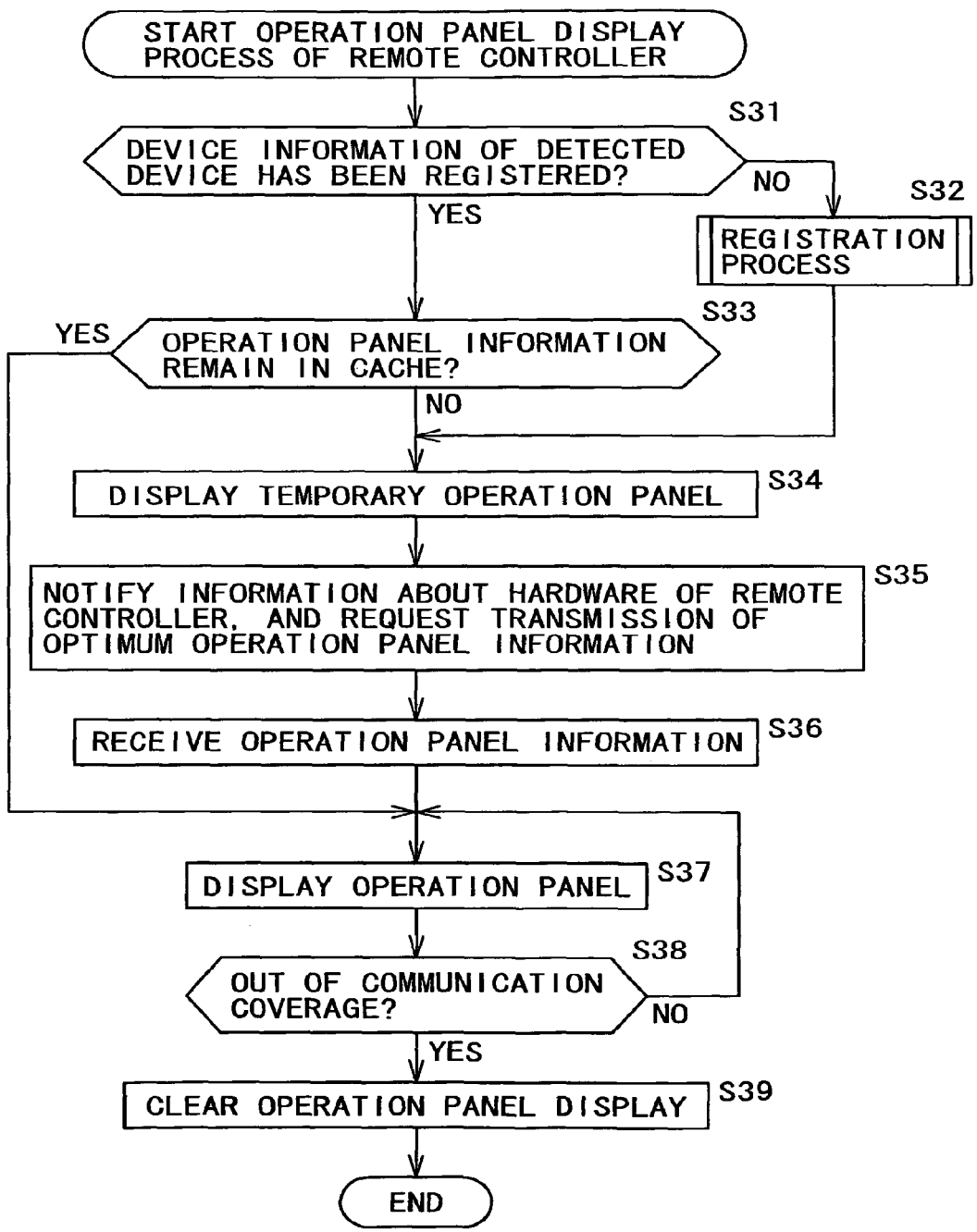
FIG. 16 is a flow chart for explaining a process of a remote controller that displays an operation panel.

Returning to the description of FIG. 16, in step S35, the device control section 162 sends device feature information indicating features of the remote controller 1, and requests the remote controller 1 to send optimal operation panel information. For example, if the television receiver 21 is detected, as the feature information of the remote controller 1, information about a hardware such as a resolution (the screen size) of the LCD 51 is sent to the television receiver 21, and transmission of the operation panel information in accordance with the resolution of the LCD 51 is requested.

In the television receiver 21, for example, from a plurality of the device information previously prepared, information in accordance with the resolution of the remote controller requesting the device information is selected, or a conversion process in accordance with the resolution of the remote controller is performed.

In response to a request from the remote controller 1, the device sends the operation panel information in accordance with the hardware configuration of the remote controller 1 through Bluetooth communication. Therefore, in step S36, the device control section 162 receives the sent operation panel information. The operation panel information received by the device control section 162 is acquired by the operation panel information acquisition section 201 of the display control section 153.

The operation panel information acquired by the operation panel information acquisition section 201 is subjected to a predetermined editing by the editing section 202, and then supplied to the control section 203. For example, if operation panel information is obtained from a plurality of device, a predetermined editing of an HTML file (operation panel information) is performed in the editing section 202, in order to display a plurality of operation panels on the LCD 51.

In step S37, the control section 203 causes the LCD 51 to display the operation panels.

FIG. 18 is a diagram showing an example of an operation panel to be displayed on the basis of the operation panel information sent from the television receiver 21.

In the example of FIG. 18, a power button 321 is displayed on the upper right of the operation panel, and a switching button 322 to be operated when switching sources among broadcasting satellite (BS) digital broadcasts, communication satellite (CS) digital broadcasts, and analog broadcasts are displayed on the left hand of the power button 321. In addition, a numeric keypad 323 is displayed below the switching button 322, and a mute button 324 to be operated when turning off the volume output, a volume button 325 to be operated when adjusting the volume, and a channel switching button 326 to be operated when switching the channels are displayed on the right hand of the numeric keypad 323.

As apparent by comparison with the temporary operation panel shown in FIG. 17, the operation panel shown in FIG. 18, which is displayed on the basis of the information sent from the television receiver 21, is customized in accordance with the function of the television receiver 21. In other words, if the television receiver 21 has the function of displaying programs of BS digital broadcasts, CS digital broadcasts, analog broadcasts, etc., the operation panel, on which buttons for switching these broadcasts, etc. are prepared as shown in the operation panel of FIG. 18, is displayed on the basis of the operation panel information sent from the television receiver 21. The user of the remote controller 1 can operate the television receiver 21 by utilizing the operation panel.

Here, the operation panel information (the HTML file) for displaying the operation panel shown in FIG. 18 is remained in the cache memory 69A.

Returning to the description of FIG. 16, the radio field intensity detection section 205 of the display control section 153 determines whether or not the remote controller 1 goes out of the communication coverage with devices. Until it is determined that it is out of the communication coverage, the process returns to step S37 to continue the display of the operation panel. From the communication control section 151 for controlling communication between the Bluetooth module 67 and the device, the radio field intensity detection section 205 is informed of the receiving condition of radio waves used in this communication.

If determined in step S38 that the remote controller 1 is out of the communication coverage, for example, because the user, who was operating the television receiver 21 until then, moves along with the remote controller 1, the process advances to step S39, in which the control section 203 erases the display of the operation panel that was displayed until then.

Figure 19:
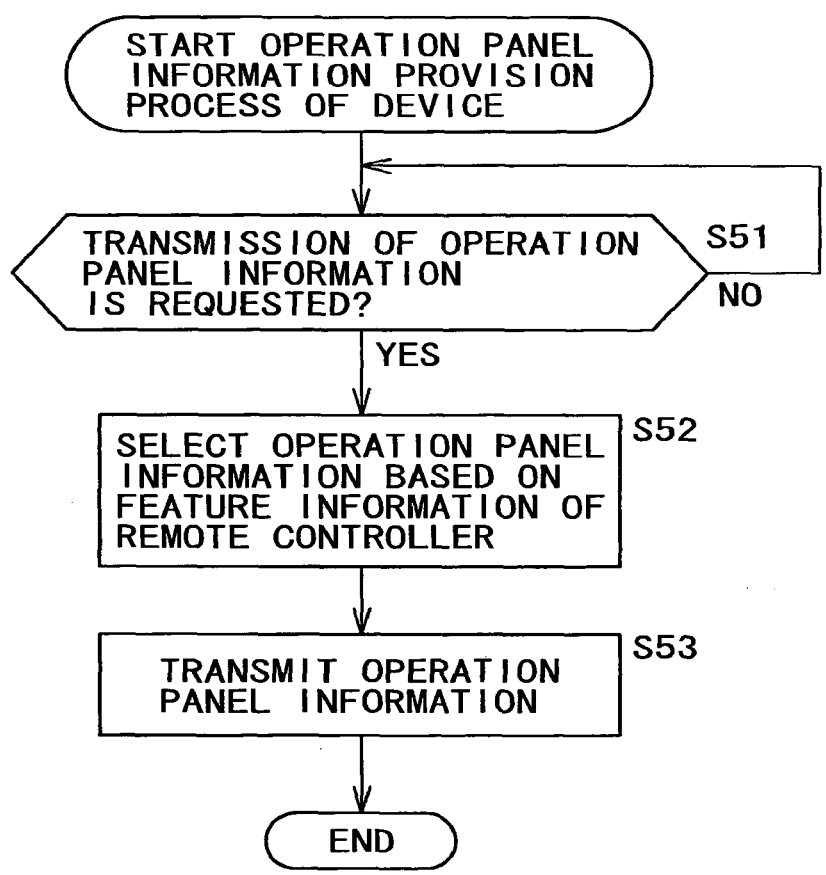
FIG. 19 is a flow chart for explaining a process executed by a device in response to the process of FIG. 16.

Referring to the flow chart of FIG. 19, a description will next be made of a process, which is executed by the television receiver 21 as a device, in response to the process of FIG. 16.

In step S51, based on the information to be received in the Bluetooth module 229 and then supplied via the communication control section 242, the operation panel information management section 243 of the television receiver 21 determines whether or not transmission of operation panel information is requested, and waits until it determines that the transmission is requested.

If the operation panel information management section 243 determines in step S51 that the transmission of the operation panel information is requested, the process advances to step S52 to select the operation panel information to provide, on the basis of the feature information of the remote controller 1 (the resolution of the LCD 51, and the information indicating whether color display is possible or not), which is contained in the request from the remote controller 1.

For example, in the case where a plurality of the operation panel information corresponding to their respective resolutions are prepared in the television receiver 21, one corresponding to the resolution of the remote controller 1 is selected from these information. Further, the operation panel information management section 243 converts the display size of the operation panel information to select, as operation panel information provided, one corresponding to the resolution of the remote controller 1. The operation panel information selected by the operation panel information management section 243 is outputted to the communication control section 242.

In step S53, the communication control section 242 sends the remote controller 1 the operation panel information selected by the operation panel information management section 243. Based on the operation panel information sent as above, an operation panel is displayed in the remote controller 1 (step S37 in FIG. 16).

Thus, there is the selected operation panel information in accordance with the features such as the resolution and the capability of color display in the remote controller 1. This enables to have the remote controller 1 display the optimal operation panel.

By the foregoing process, only by bringing the remote controller 1 close to a device that a user desires to operate, the user can cause the operation panel of the device to be displayed automatically, and also cancel the display without performing for himself/herself any operation for canceling the display of the operation panel.

Additionally, since the operation panel displayed on the remote controller 1 is to be displayed on the basis of the information sent from the device, it is capable of displaying the optimal operation panel in accordance with the function of the device, and also controlling the device by utilizing this operation panel.

In other words, in a state in which the operation panel shown in FIG. 18 is displayed on the LCD 51, for example, a user can control the on/off of the power of the television receiver 21 by operating the power button 321.

While the foregoing description has been made of the case where the device that can be controlled by the remote controller 1 is placed near the remote controller 1, and the device can communicate directly with the remote controller 1 by Bluetooth, it may be configured such that other device to be connected via a network to the device that can communicate directly is also controlled indirectly by the remote controller 1.

Figure 20:
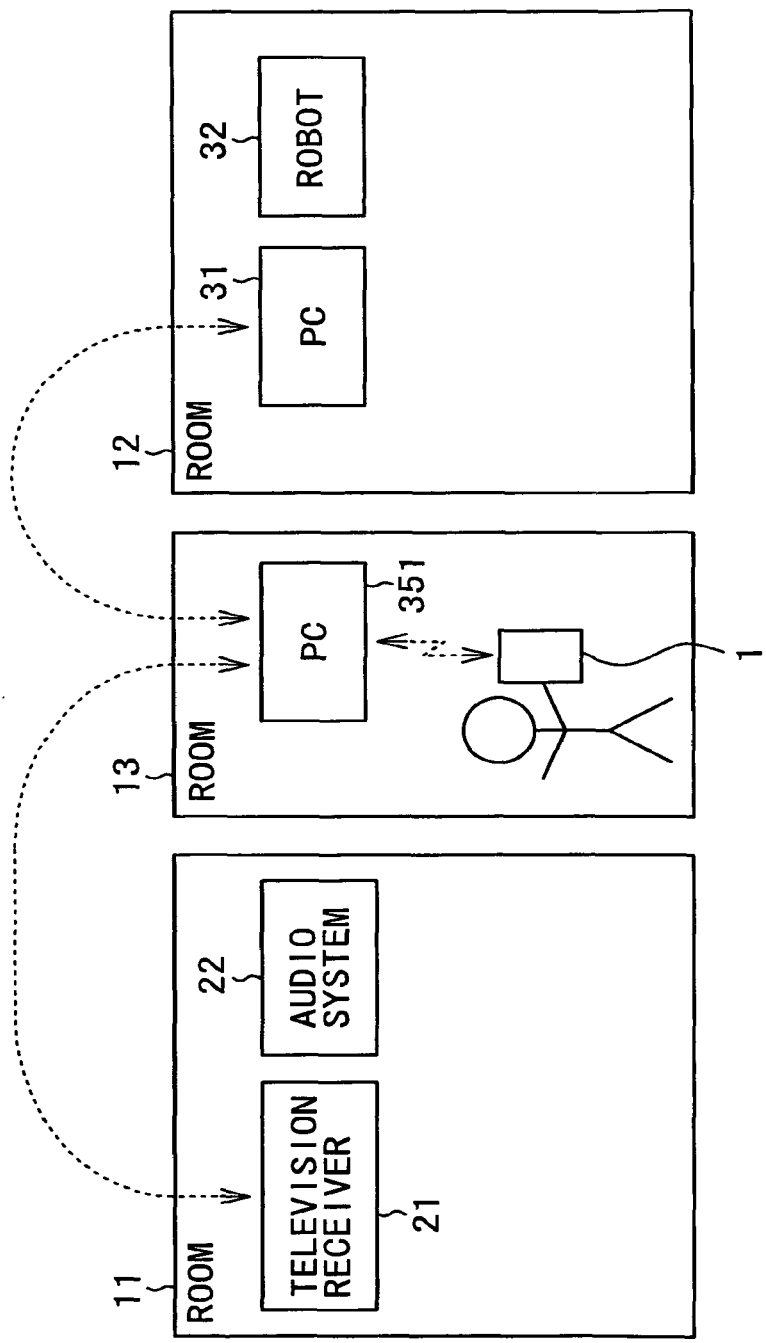
FIG. 20 is a diagram showing an example of a configuration of other control system to which the present invention is applied.

FIG. 20 is a diagram showing an example of a configuration of other control system to which the present invention is applied. In FIG. 20, the same parts as in FIG. 1 bear the same references.

In FIG. 20, a room 13 is added to the configuration of FIG. 1, and a personal computer 351 is placed there. Like other devices, the personal computer 351 has the configuration in FIG. 10 and FIG. 11. That is, like the television receiver 21 and the audio system 22, a user can operate the personal computer 351 by using the remote controller 1.

By a wireless LAN in accordance with IEEE802.11b, for example, the personal computer 351 is connected to the television receiver 21 placed at the room 11, and the personal computer 31 placed at the room 12. In FIG. 20, an arrow of broken line linking the personal computer 351 and the television receiver 21, and an arrow of broken line linking the personal computer 351 and the personal computer 31 indicate that it is possible to mutually communicate via the wireless LAN.

In the control system of FIG. 20, the user holding the remote controller 1 is present at the room 13. Therefore, by the process described by referring to FIG. 12, for example, the personal computer 351 is detected, and device information thereof is registered. Thereafter, the remote controller 1 requests to the personal computer 351 the information about devices that can be controlled indirectly via the personal computer 351.

For example, the television receiver 21 and the personal computer 31, which are connected via the wireless LAN to the personal computer 351, can be regarded as a device that can be controlled indirectly via the personal computer 351.

Accordingly, in response to a request from the remote controller 1, the address information of the television receiver 21 and the personal computer 31, such as IP addresses and media access control (MAC) addresses are sent from the personal computer 351 to the remote controller 1, as the information about controllable devices.

Thereafter, based on the obtained address information, the remote controller 1 accesses to the television receiver 21 and the personal computer 31 via the personal computer 351, so that the remote controller 1 obtains the operation panel information of the television receiver 21 and the personal computer 31. Based on the obtained operation panel information, for example, the operation panel of the personal computer 31 is displayed on the LCD 51. Therefore, even staying at the room 13 the user can operate it to control the personal computer 31 placed at the room 12.

Specifically, when the operation panel of the personal computer 31 is operated, a command corresponding to the user operation is created in the remote controller 1, and the created command is sent by Bluetooth communication to the personal computer 351. Upon receipt of the command sent by the Bluetooth communication, the personal computer 351 sends the personal computer 31 placed at the room 12, via the wireless LAN, the command sent from the remote controller 1, on the basis of the information which is contained in the command and indicates the transmission destination of the command such as an IP address. The personal computer 31, which has obtained the command, performs an operation in accordance with the command.

Thus, in the control system of FIG. 20, even to the device that cannot make direct communication with the remote controller 1, the user can control it via the device that can make direct communication (the personal computer 351) and the network (the wireless LAN).

Figure 21:
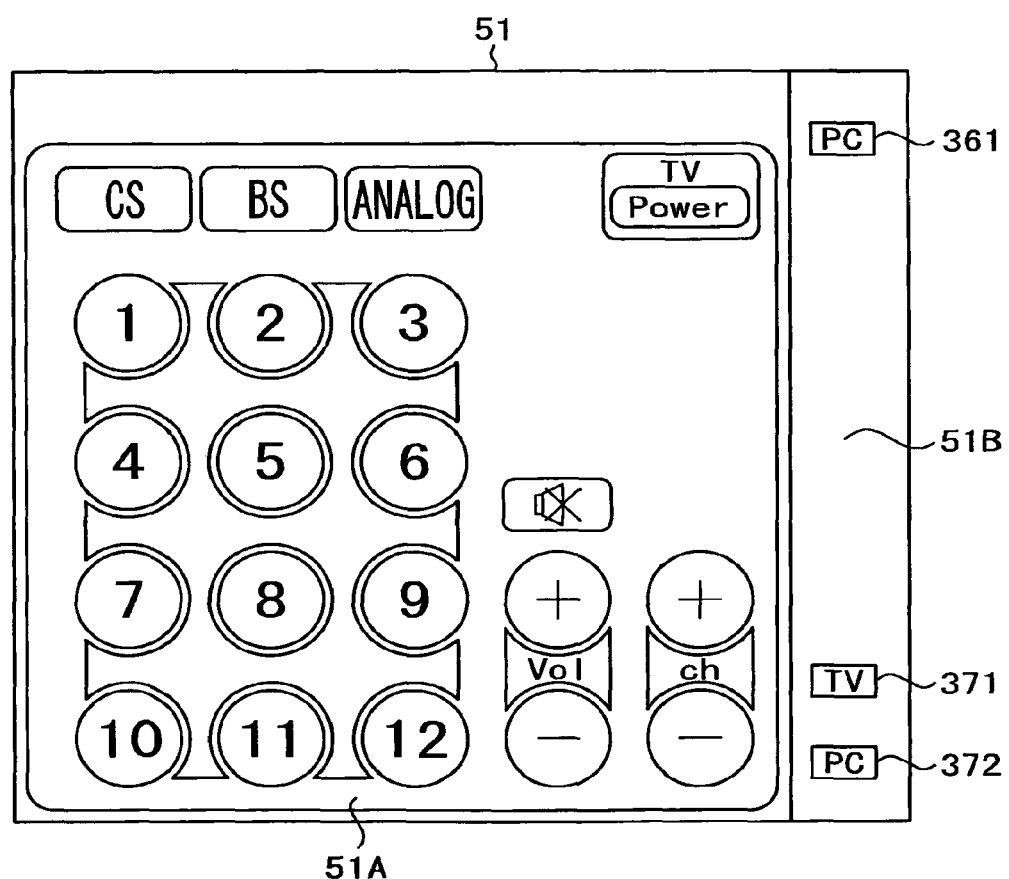
FIG. 21 is a diagram showing an example of display of an operation panel.

FIG. 21 is a diagram showing an example of display of the LCD 51 when the remote controller 1 is in the state shown in FIG. 20.

The operation panel displayed on a region 51A of FIG. 21 is to be displayed on the basis of the operation panel information obtained from the television receiver 21 via the wireless LAN, the personal computer 351, and the Bluetooth communication.

In an upper part of a region 51B of FIG. 21, there is displayed an icon 361 to be operated when instructing it to display the operation panel of the personal computer 351, which is a device that can communicate directly by Bluetooth communication. In a lower part of the region 51B, there are displayed an icon 371 to be operated when instructing it to display the operation panel of the television receiver 21 and an icon 372 to be operated when instructing it to display the operation panel of the personal computer 31, which are able to be controlled indirectly via the personal computer 351

In the state of FIG. 21, the user can instruct with the icon 361 so as to display the operation panel of the personal computer 351, and instruct with the icon 372 so as to display the operation panel of the personal computer 31. Here, FIG. 21 is taken to be an example of the case where the user sets to display one operation panel on the LCD 51.

The user can operate the television receiver 21 and the personal computer 31 by utilizing the operation panel so displayed. Hence, the user can control the personal computer 31 located at other room, without bringing the remote controller 1 close to the device.

The operation of the control system of FIG. 20 will next be described.

Figure 22:
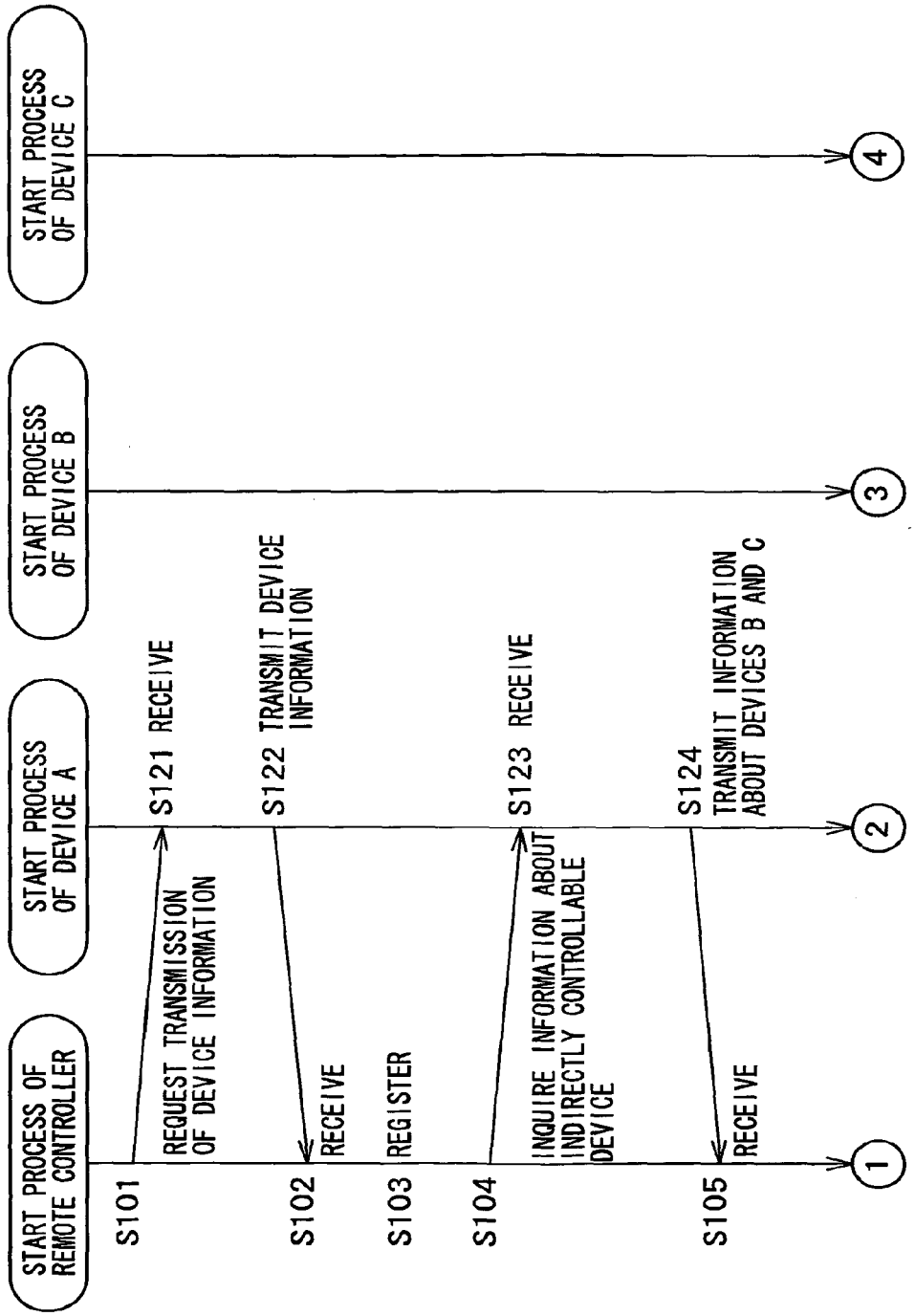
FIG. 22 is a flow chart for explaining an operation of the control system in FIG. 20.
Figure 23:
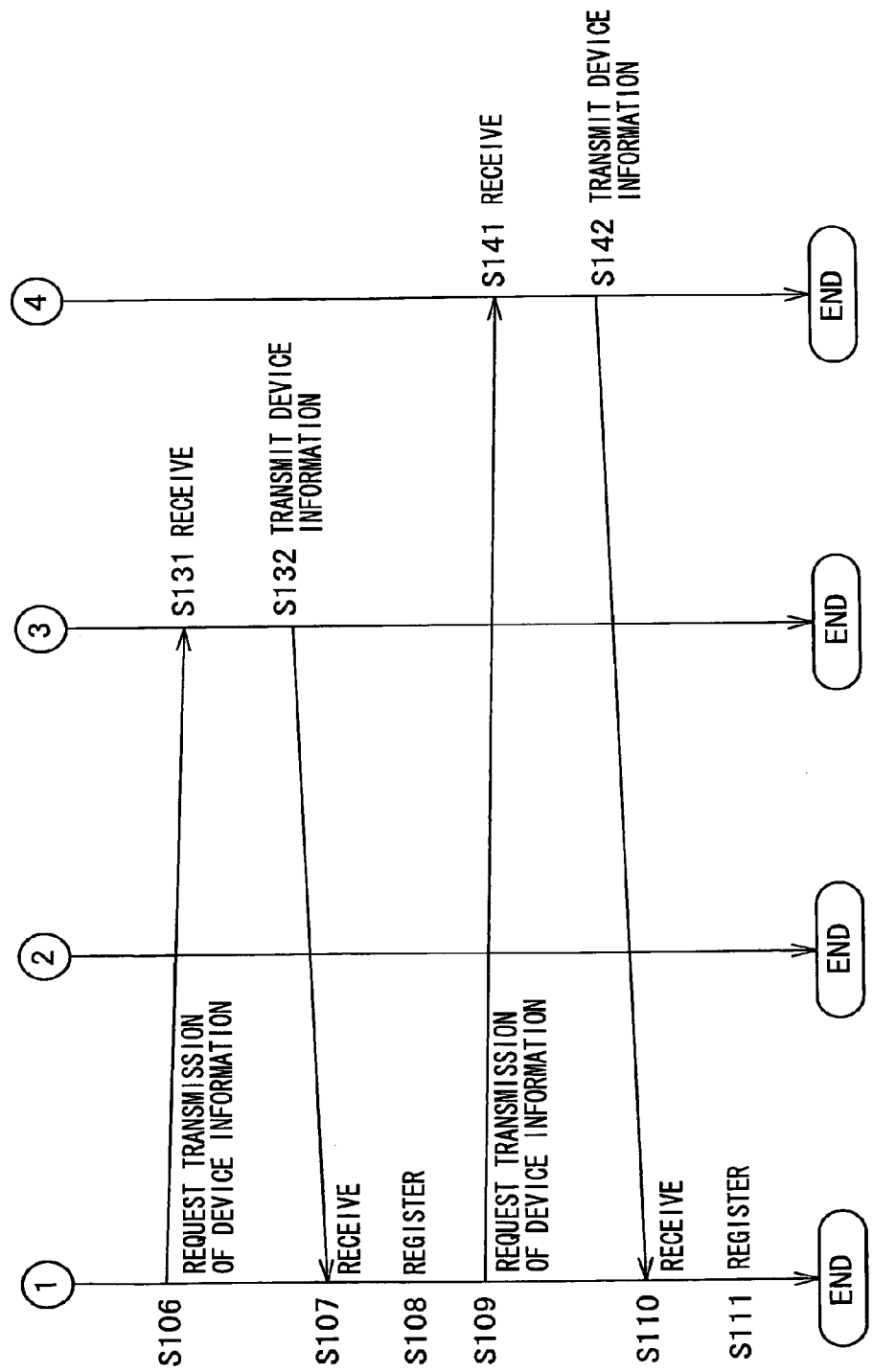
FIG. 23 is a flow chart, continued from FIG. 22, for explaining the operation of the control system in FIG. 20.

Referring to the flow charts of FIGS. 22 and 23, a description is first made of a process for registering device information in the remote controller 1 in the control system of FIG. 20. In the following, for the purpose of convenience, the personal computer 351 of FIG. 20 is referred to as a "device A", the television receiver 21 as a "device B", and the personal computer 31 as a "device C".

In step S101, the remote controller 1 requests the device A (the personal computer 351) detected by search to send the device information. The process between the remote controller 1 and the device A is basically the similar as the process described by referring to FIG. 12 and FIG. 15, and the like, which process is to request the device A waiting for registration to send the device information of the device A.

The request from the remote controller 1 is received by the device A in step S121. The device information of the device A is sent from the device A to the remote controller in step S122.

In step S102, the remote controller 1 receives the device information sent from the device A, and the process advances to step S103 to register it. By this means, there is registered the information such as a device ID, a manufacturer code, a Bluetooth address of the device A.

In step S104, the remote controller 1 inquires of the device A information about the devices that can be controlled indirectly by interposing the device A.

This inquiry is received by the device A in step S123, and the process advances to step S124 to send the remote controller 1 address information such as the IP addresses on the wireless LAN, which are allocated to the device B and the device C.

For example, when the connection by the wireless LAN is established, the personal computer 351 as the device A has obtained information such as IP addresses of the television receiver 21 and the personal computer 31, this information is then sent to the remote controller 1. The above-mentioned IP addresses are to be allocated by a router (not shown).

In step S105, the remote controller 1 receives the information sent from the device A.

In step S106, based on the information notified from the device A, the remote controller 1 sends the device A a message for requesting the device B to send the device information. This message contains information such as the IP address of the device B that is the television receiver 21, as information designating a transmission destination.

The message is received by the device A via Bluetooth, and then sent via the device A to the device B. That is, based on the IP address contained in the message, the device A determines the transmission destination of the message and sends it to the device B.

The device B receives the message sent via the device A in step S131, and the process advances to step S132 to send the device information of the device B, in response to a request from the remote controller 1. The device information sent from the device B is sent via the device A to the remote controller 1.

In step S107, the remote controller 1 receives the device information sent from the device B via the device A, and the process advances to step S108 to register it.

Then, the process advances to step S109, in which the remote controller 1 sends a message for requesting the device C to send the device information. Like the message to the device B, the message to the device C is sent via the device A to the device C.

In step S141, the device C receives the message sent from the remote controller 1, and the process advances to step S142 to send the device information of the device C to the remote controller 1.

In step S110, the remote controller 1 receives the device information sent from the device C via the device A, and the process advances to step S111 to register it.

By the foregoing process, the device information of the device A that can communicate directly, and the device information of the device B and the device C, each of which can communicate indirectly, are registered in the remote controller 1.

FIG. 24 is a diagram showing an example of the device information that are registered in the remote controller 1 by the process described by referring to FIG. 22 and FIG. 23.

In the example of FIG. 24, the device information of the personal computer 351 is registered as first information (device 1), and the device information of the television receiver 21 is registered as second information (device 2), and the device information of the personal computer 31 is registered as third information (device 3).

Particularly, "personal computer" in the name, "PC" in the category, "00x1" in the manufacturer code, "1122" in the device ID, and "06:00:25:63:75:B5" in the Bluetooth address are registered as the device information of the personal computer 351. Also, "television" in the name, "TV" in the category, "00x1" in the manufacturer code, "1234" in the device ID, and "08:00:46:21:94:A3" in the Bluetooth address are registered as the device information of the television receiver 21. Further, "personal computer" in the name, "PC" in the category, "00x5" in the manufacturer code, "7788" in the device ID, and "07:01:22:34:56:78" in the Bluetooth address are registered as the device information of the personal computer 31.

The information such as the addresses of the respective devices, which were obtained from the device A, is also registered along with the device information of FIG. 24.

FIG. 25 is a diagram showing an example of information to be registered in the remote controller 1, together with the device information.

As shown in FIG. 25, there are registered the IP address and the MAC address of the personal computer 351 (the device A), and the respective IP addresses and the MAC addresses of the television receiver 21 (the device B) and the personal computer 31 (the device C), which were notified from the device A.

In the example of FIG. 25, the IP address of the television receiver 21 is "192.168.0.10", and the MAC address is "00-30-65-BA-E9-C2". The IP address of the personal computer 351 is "192.168.0.2", and the MAC address is "00-30-63-CA-E8-D1". The IP address of the personal computer is "192.168.0.11", and the MAC address is "00-30-65-CC-E9-05".

Further in FIG. 25, there is also registered information indicating the relationship of connection (parentage) when the respective devices are viewed from the remote controller 1. Concretely, it indicates that the device corresponding to the parent of the television receiver 21, and the device corresponding to the parent of the personal computer 31 are the personal computer 351. Here, the device that can communicate directly with the remote controller 1 is taken to be a "parent" device, and the device that can communicate indirectly with the remote controller 1 by interposing the "parent" device is taken to be a "child" device.

By referring to the information shown in FIG. 24 and FIG. 25, the remote controller 1 can send a predetermined command to a device connected indirectly. Accordingly, thereafter, the sending/receiving of various data between the remote controller 1 and the television receiver 21, and the sending/receiving of various data between the remote controller 1 and the personal computer 31 are performed by way of the personal computer 351, as shown in FIG. 22 and FIG. 23.

Figure 26:
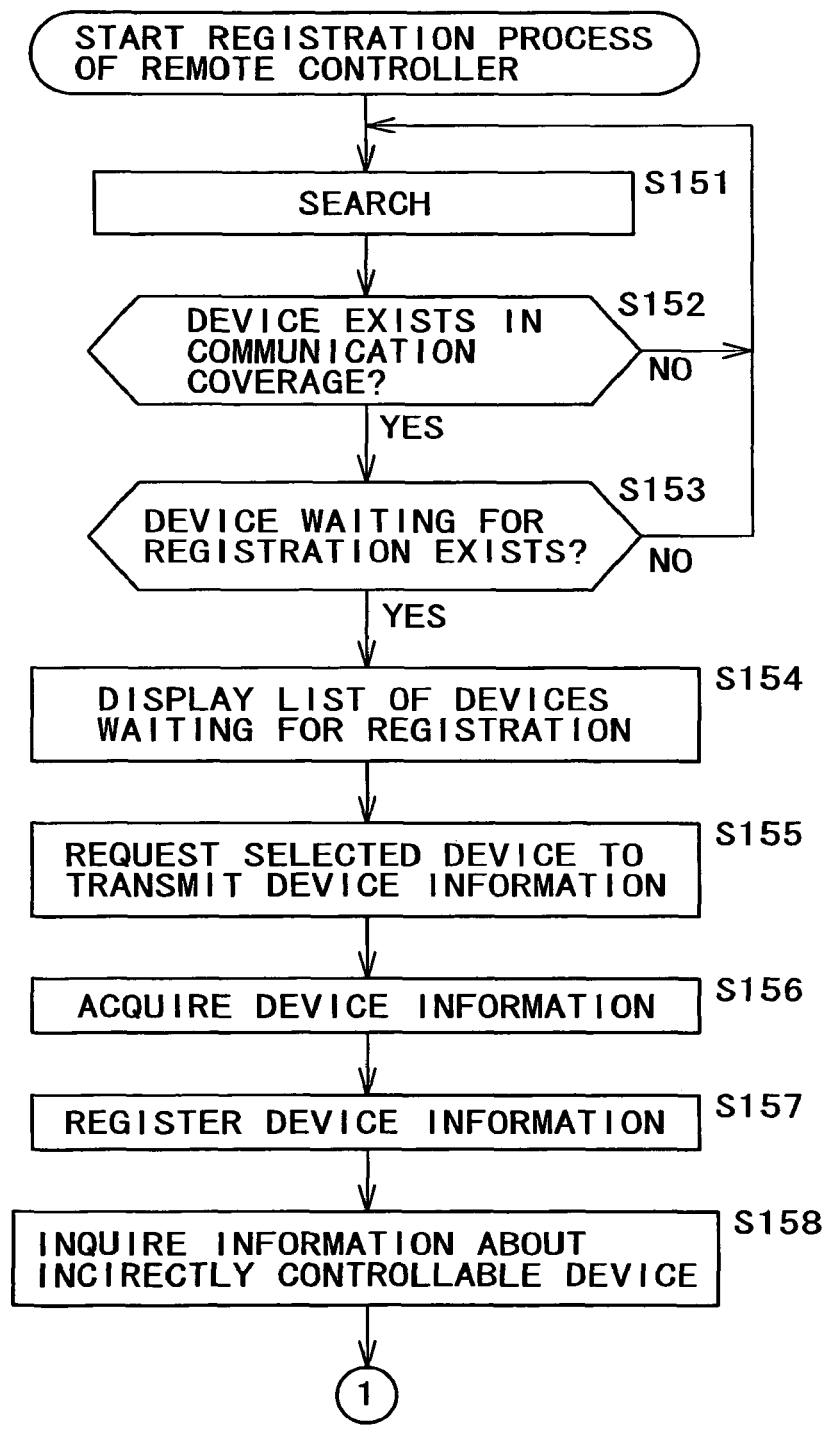
FIG. 26 is a flow chart for explaining a registration process of a remote controller.

Referring to FIG. 26 and FIG. 27, a description will next be made of the process in the remote controller 1 of FIG. 20, in order to register the device information.

FIG. 26 and FIG. 27 are intended for explaining more detailed process in the remote controller 1 described with reference to FIG. 22. The process of FIG. 26 is basically the similar as the process described with reference to FIG. 12.

The processes from step S151 to step S157 are the similar as the process in step S1 to step S7 in FIG. 12. That is, when a user instructs to register the device information, the search section 161 activates the Bluetooth module 67 to make search (inquiry and page) of devices in step S151.

If the search section 161 determines in step S152 that devices is present in the communication coverage, the process advances to step S153 to determine whether or not there is a device waiting for registration among the devices detected by search. For example, if the device A (the personal computer 351) is set to the registration wait state, the search section 161 determines in step S153 that there is a device waiting for registration, and the process advances to step S154.

In step S154, the display control section 153 causes the LCD 51 to display a list of devices waiting for registration. In step S155, the device control section 162 requests transmission of device information, for example, of the device A on the list, which is instructed to register the device information. In response to the request from the remote controller 1, the device information is readout in the device A, and the read device information is provided to the remote controller 1 by Bluetooth communication.

In step S156, the device control section 162 obtains the device information sent from the device. In step S157, the device information management section 181 registers the device information of the device A obtained by the device control section 162.

In step S158, the request section 163 inquires of the device A information about devices, to which indirect control (the control via the device A) is executable.

Since the device A, in response to this inquiry, notifies the presence/absence of indirectly controllable devices, the request section 163 determines in step S159 whether indirectly controllable devices are present or not.

If the request section 163 determines in step S159 that indirectly controllable devices are present, the process advances to step S160 to receive the address information, which is sent from the device A, about the device B and the device C that are indirectly controllable devices. On the other hand, if determined in step S159 that no indirectly controllable device is present, the process is terminated.

The address information obtained by the request section 163 is outputted to the device information management section 181, and managed together with the device information by the device information management section 181.

In step S161, the device control section 162 sends the device A a message for requesting, for example, the device B to send device information. This message contains the IP address of the device B, as the information indicating the transmission destination of the message. Since the device information is sent from the device B in response to the message, the device control section 162 receives it in step S162.

The message sent from the remote controller 1, and the device information sent from the device B are sent/received by way of the device A.

In step S163, the device information management section 181 registers the device information of the device B, and the process advances to step S164 to determine whether or not there is registered all the device information of devices notified as being indirectly controllable.

If the device information management section 181 determines in step S164 that there is not registered all the device information of the devices notified as being indirectly controllable, the process returns to step S161 to execute repetitively the foregoing process.

If the device information management section 181 determines in step S164 that there is registered all the device information of the devices notified as being indirectly controllable, the process is terminated.

Figure 28:
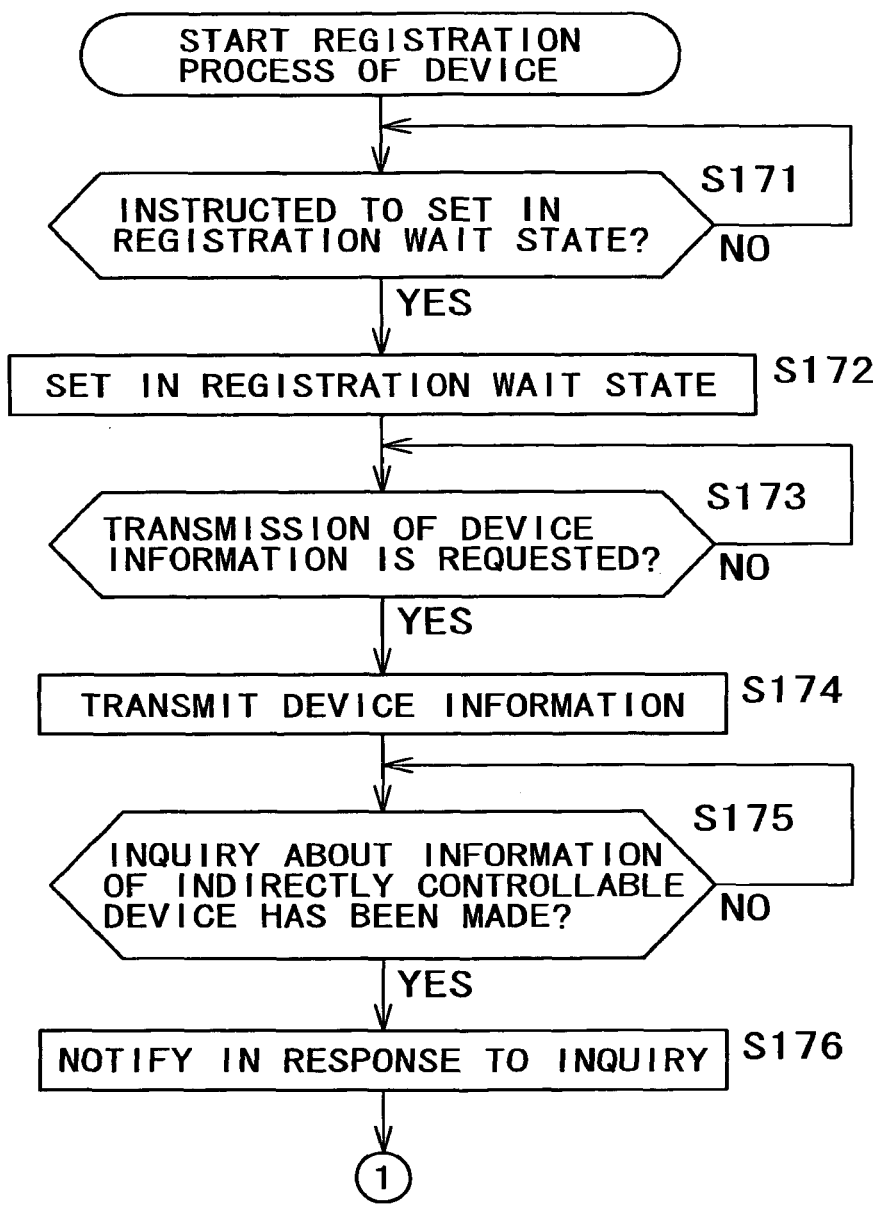
FIG. 28 is a flowchart for explaining a process executed by a device in response to the process of FIG. 26 and FIG. 27.
Figure 29:
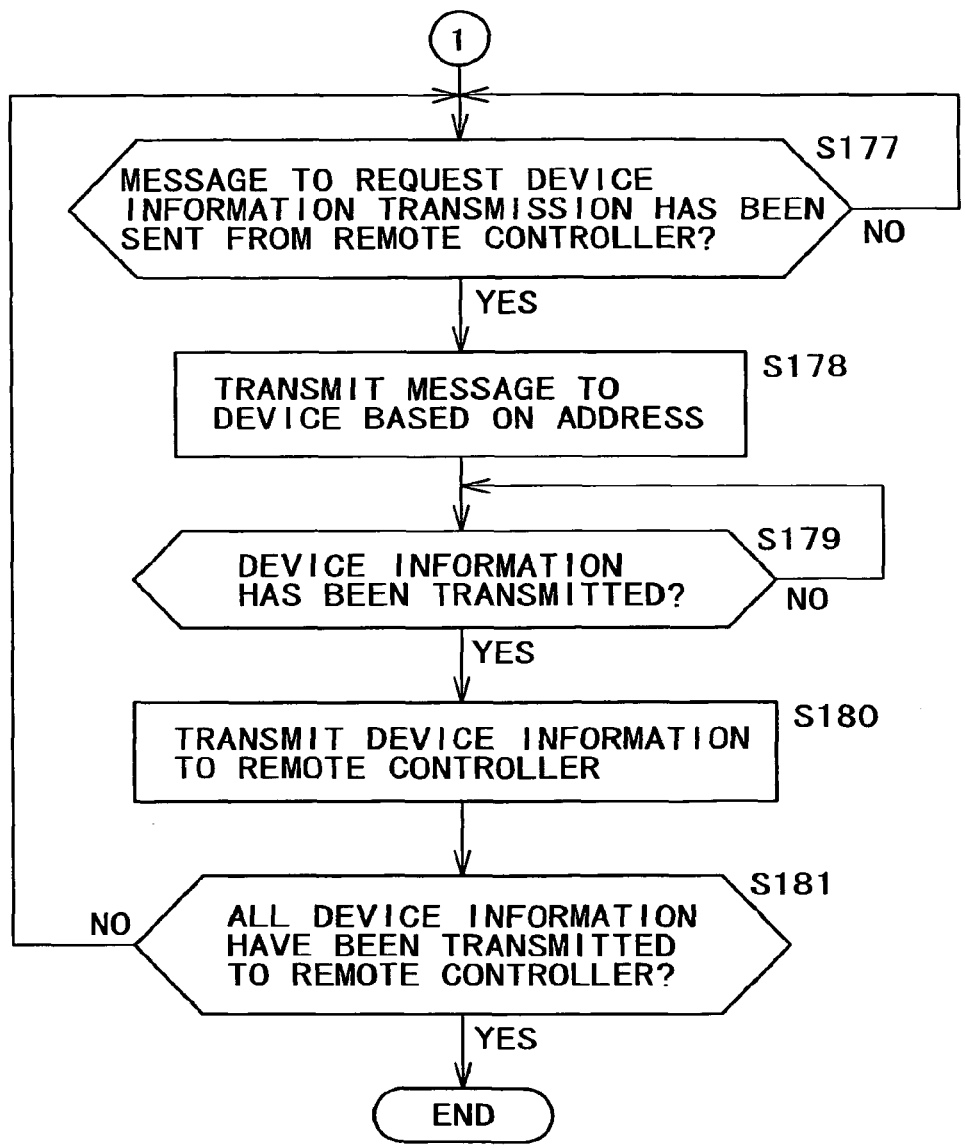
FIG. 29 is a flow chart for explaining the process continued from FIG. 28, which is executed by a device in response to the process of FIG. 26 and FIG. 27.

Referring to the flow charts of FIG. 28 and FIG. 29, a description will next be made of the process of a device, which is executed in response to the process in FIG. 26 and FIG. 27. Here, a description is made of the process in the device A, which can communicate directly with the remote controller 1 by Bluetooth.

Figure 15:
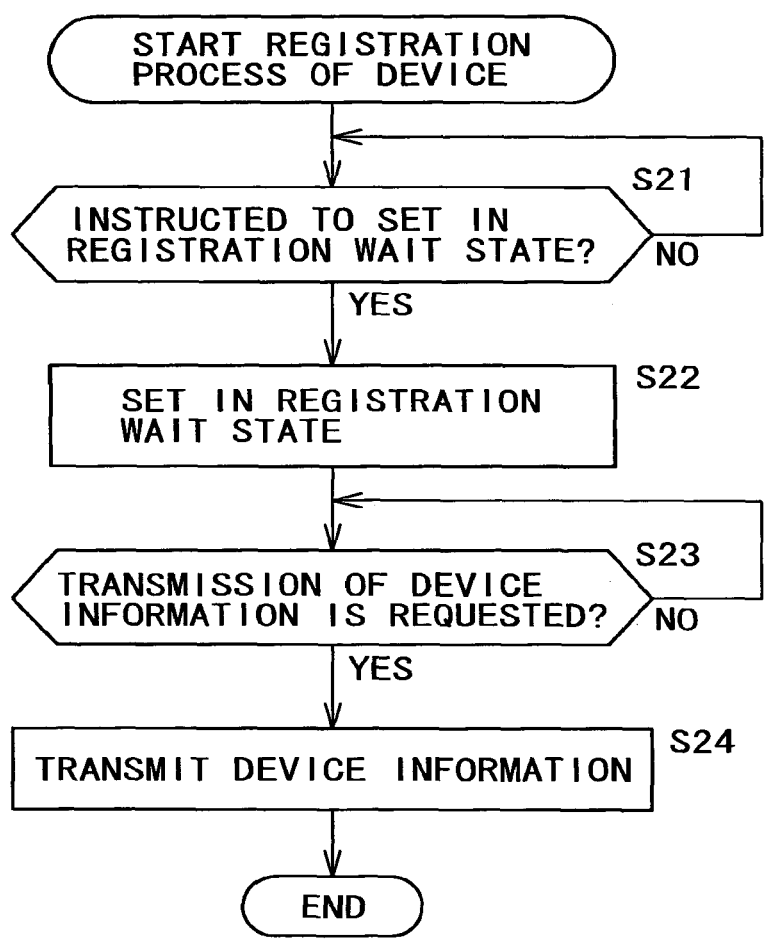
FIG. 15 is a flowchart for explaining a process executed by a device in response to the process of FIG. 12.

The processes in steps S171 to S174 are the similar as the process in steps S21 to S24 of FIG. 15. That is, in step S171, if the control section 241 of the personal computer 351 determines that it is instructed to set to the registration wait state, the process advances to step S172 to set the status of the device A to the registration wait state. Further, if the communication control section 242 determines in step S173 that the remote controller 1 requests transmission of device information, the process advances to step S174 to send the device information managed by the device information management section 244.

In step S175, the control section 241 determines whether or not there is an inquiry about information of indirectly controllable devices, and waits until it determines that there is the inquiry. As described above, the remote controller 1 inquires of the device A, which can communicate directly, about information of devices that can be controlled via the device A (step S158 in FIG. 26).

If the control section 241 determines in step S175 that there is an inquiry about the information of devices, the process advances to step S176 to send the address information of the device B and the device C, from the communication control section 242 to the remote controller 1. When the wireless LAN is established between the device B and the device C, the control section 241 obtains previously the information of the IP address and the like of the device B and the device C.

Thereafter, a message for requesting the device B and the device C to send device information is to be sent from the remote controller 1 by Bluetooth. Therefore, the communication control section 242 determines in step S177 whether this message reaches or not, and waits until it determines that this message reaches.

If the communication control section 242 determines in step S177 that a message bound for the device B or the device C reaches, the process advances to step S178 to refer to address information contained in the message, and send the message sent from the remote controller 1 via wireless LAN, to the device designated by the address information.

For example, if the IP address of the device B is contained as information indicating the destination of the message, the communication control section 242 sends the device B a message for requesting transmission of device information.

Since the device, which has received the message via wireless LAN, sends the device information to the remote controller 1, the communication control section 242 determines in step S179 whether the device information reaches or not.

If the communication control section 242 determines in step S179 that the device information reaches, the process advances to step S180 to send it to the remote controller 1 by Bluetooth. The device information sent from the device contains, as its destination, for example, identification information such as the Bluetooth address of the remote controller 1.

The communication control section 242 determines in step S181 whether or not all of the device information about indirectly controllable devices are sent to the remote controller 1. If determined that it does not reach, the process returns to step S177 to execute the process from there repetitively.

On the other hand, if the communication control section 242 determines in step S181 that all the device information about indirectly controllable devices are sent to the remote controller 1, the process is terminated.

By the foregoing process, the remote controller 1 obtains the device information of the device that can communicate directly with the remote controller 1, and of the devices that can communicate indirectly via the former device. Based on the obtained device information, the remote controller 1 can send a predetermined command even to the devices that cannot communicate directly.

Figure 30:
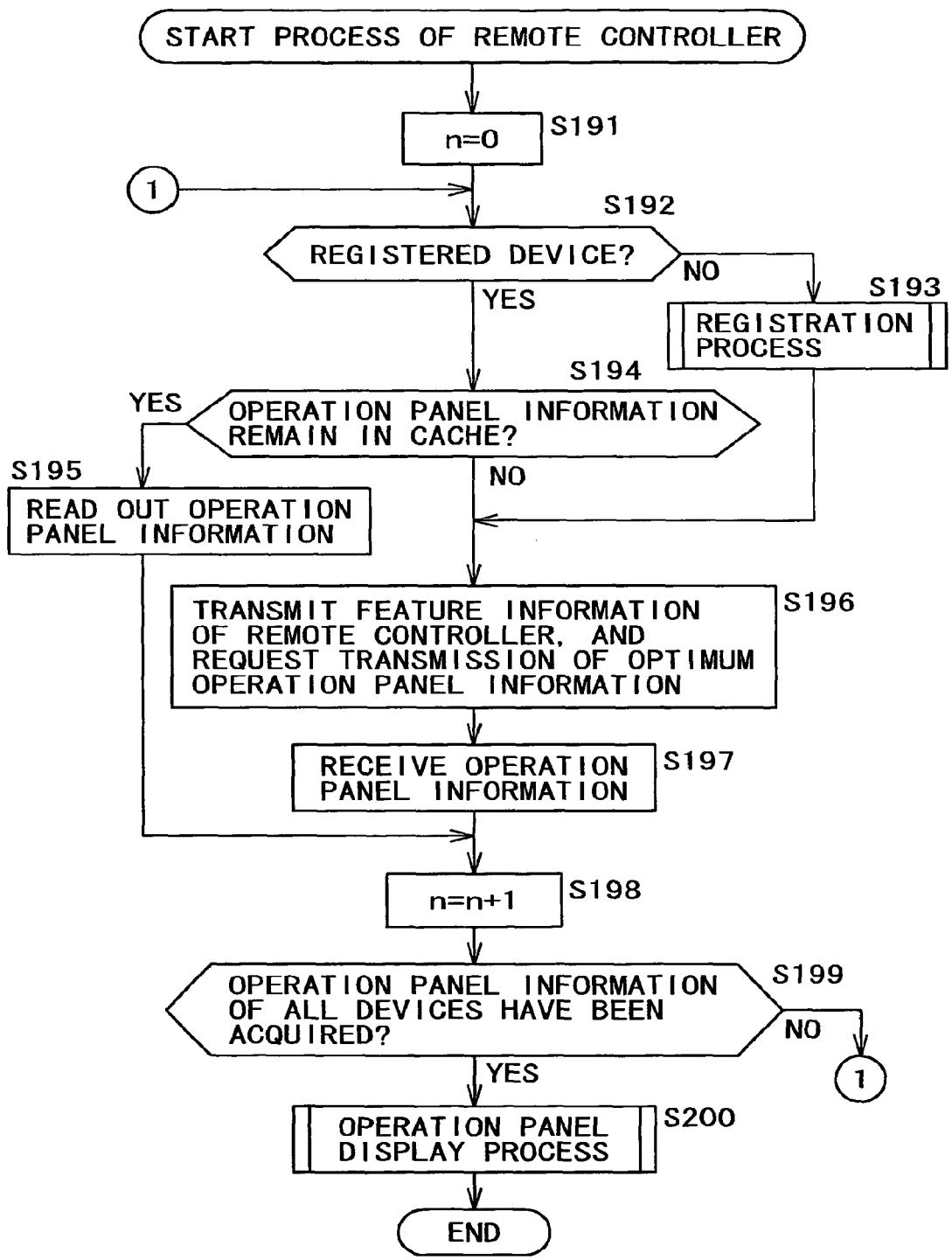
FIG. 30 is a flow chart for explaining a process of a remote controller that displays an operation panel.

Referring to the flow chart of FIG. 30, a description will next be made of the process in the remote controller 1, when a plurality of devices are detected by search.

For example, when notified that devices are detected by search, which the search section 161 makes in a predetermined cycle, the operation panel information acquisition section 201 of the display control section 153 sets "0" to a variable n indicating a target device in step S191. The variable n is incremented one by one, every time that the operation panel information of the detected device is acquired (step S198).

In step S192, the device information management section 181 of the storage control section 152 refers to the information registered in the storage section 69, and determines whether the device information of the current target device (the device corresponding to the variable n) is already registered or not.

If the device information management section 181 determines in step S192 that the device information of the target device is not registered, the process advances to step S193 to perform the registration process of device information, which has been described with reference to FIG. 26 and FIG. 27. After the device information is registered, the process in step S194 is skipped, and the succeeding process is executed.

On the other hand, if the device information management section 181 determines in step S192 that the device information of the current target device is already registered in the storage section 69, the process advances to step S194. In step S194, the cache memory management section 182 determines whether or not the operation panel information of the target device is remained in the cache memory 69A.

If the cache memory management section 182 determines in step S194 that the operation panel information of the target device is remained in the cache memory 69A, the process advances to step S195 to read out the operation panel information from the cache memory 69A and output it to the operation panel information acquisition section 201.

On the other hand, if the cache memory management section 182 determines in step S194 that the operation panel information of the target device is not remained in the cache memory 69A, the process advances to step S196.

In steps S196 and S197, like steps S35 and S36 in FIG. 16, the feature information of the remote controller 1 is notified to the target device, and operation panel information sent in response to this notification is received.

For example, if the current target device is the device C (the personal computer 31) that can communicate indirectly via the device A (the personal computer 351), a message for requesting transmission of operation panel information containing such as the IP address of the personal computer 31 is sent to the personal computer 351. This message, like the message for requesting transmission of device information, is sent via the personal computer 351 to the personal computer 31.

In response to the message, operation panel information is sent from the personal computer 31 via the personal computer 351, so that the operation panel information acquisition section 201 acquires the operation panel information.

When the operation panel information of the target device is acquired in steps S195 and S197, the operation panel information acquisition section 201 increments the value of the variable n by one, in step S198. The process advances to step S199 to determine whether or not the operation panel information is acquired from all devices detected by search, and all indirectly controllable devices.

If determined that the operation panel information is not yet acquired from all the devices, the process returns to step S192 to execute repetitively thereafter the foregoing process for the next target device.

If the operation panel information acquisition section 201 determines in step S199 that the operation panel information is acquired from all the devices detected by search, and all the indirectly controllable devices, the process advances to step S200 to execute a process for displaying operation panel. In step S200, there is performed, for example, editing of the operation panel information acquired from all the devices, and displaying the operation panel based on the information obtained by editing.

Figure 31:
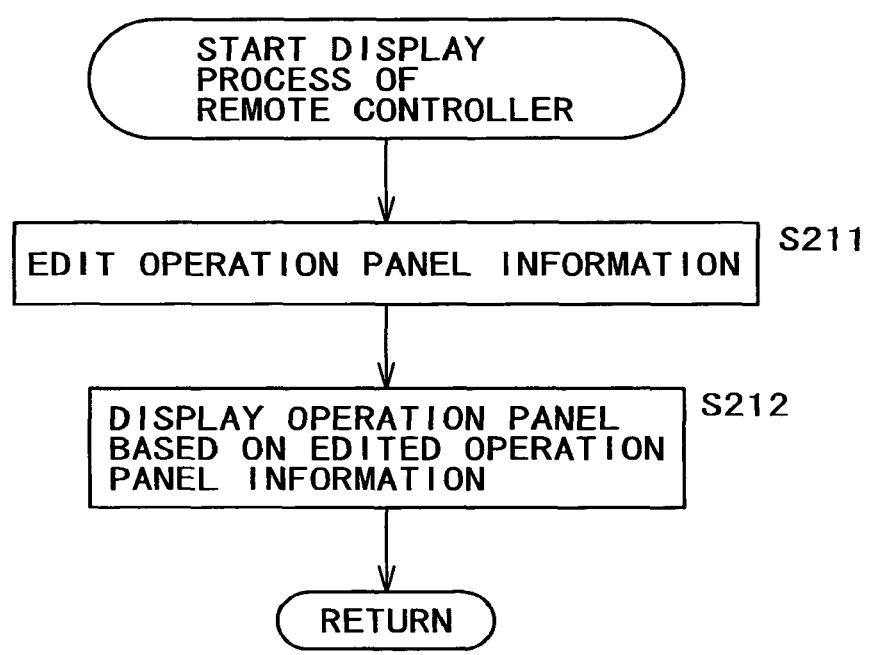
FIG. 31 is a flowchart for explaining a display process of an operation panel of a remote controller, which is executed in step S200 of FIG. 30.

Referring to the flow chart of FIG. 31, a description will next be made of an operation panel display process executed in step S200 of FIG. 30.

If a plurality of operation panel information is obtained, in step S211, the editing section 202 of the display control section 153 edits the obtained operation panel information in order to display a plurality of operation panels on the LCD 51. In FIG. 16, since it is assumed that one device is to be detected by search, one operation panel can be displayed on the entire LCD 51 on the basis of the operation panel information obtained from the detected device. In contrast, if a plurality of devices are detected, in order to display their respective operation panels on the LCD 51, it is necessary to edit based on the operation panel information obtained from the respective devices.

As editing of the operation panel information, for example, the LCD 51 is divided into a plurality of frames, and the operation panel information, which is an HTML file, is reconstituted such that the respective operation panels of the devices are displayed on their respective corresponding frames.

Figure 32:
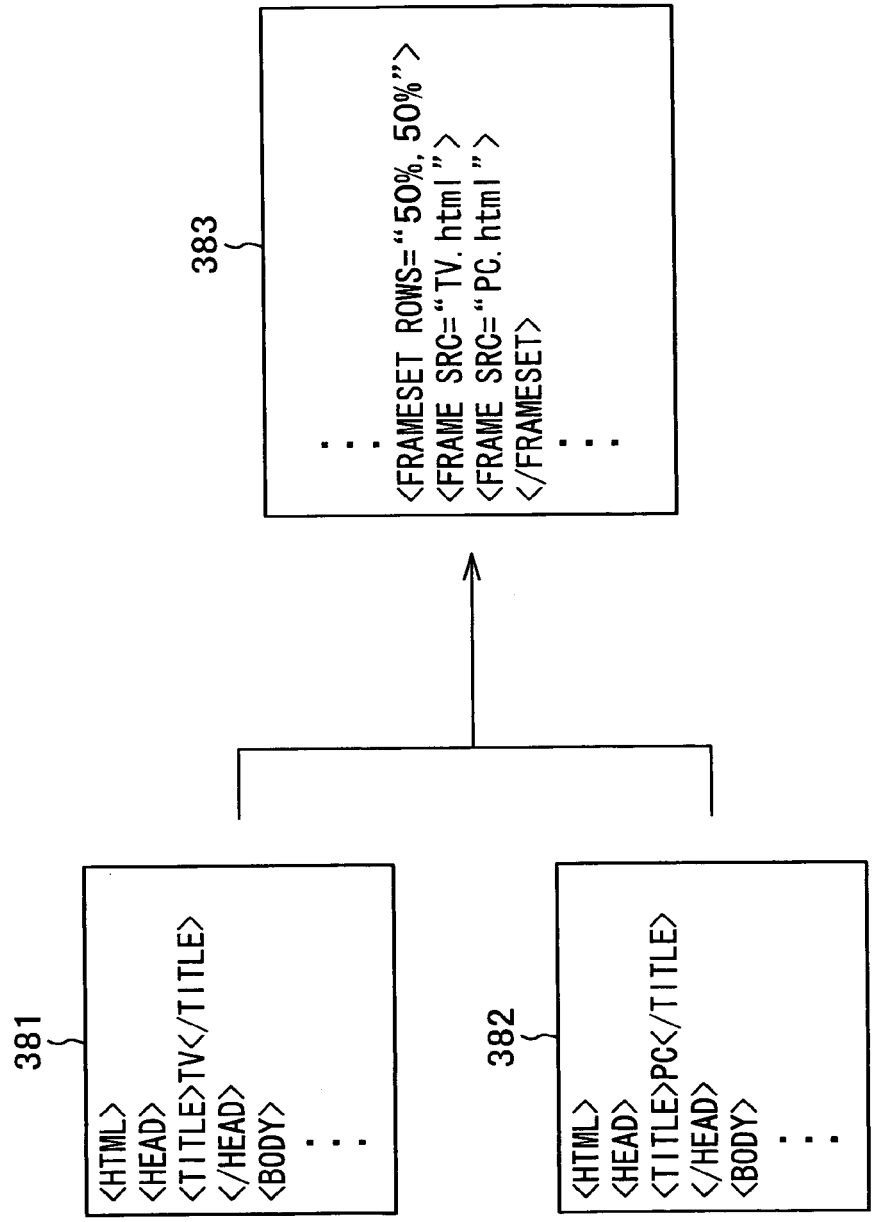
FIG. 32 is a diagram showing an example of a reconstitution of an HTML file.

FIG. 32 is a diagram showing an example of the reconstitution of the HTML files.

An HTML file 381 is the operation panel information obtained from the television receiver 21 in FIG. 20, and a "TV" is described between <TITLE> tags thereof. In FIG. 32, the HTML file 381 shows a structure of a document by each of tags of <HTML> through </HTML>, <HEAD> through </HEAD>, <TITLE> through </TITLE>, and <BODY> and the like.

An HTML file 382 is the operation panel information obtained from the personal computer 31 in FIG. 20, and a "PC" is described between <TITLE> tags thereof. The structure of the HTML file 382 has the similar structure as that of the HTML file 381.

The HTML file 381 and the HTML file 382 are obtained via the personal computer 351 from the television receiver 21 and the personal computer 31, respectively.

Based on the HTML file 381 and the HTML file 382, the editing section 202 reconstitutes the HTML files so that, for example, an HTML file 383 is newly created.

On the first line of the HTML file 383, <FRAMSET ROWS="50%, 50%"> is described. This <FRAMESET> tag defines to create upper and lower frames by horizontally dividing the LCD 51 (a browser screen) into two, each of which has size of 50%, letting the entire of the browser screen in the vertical direction be 100%.

Below the <FRAMESET> tag, <FRAM SRC="TV.html"> and <FRAM SRC="PC.html"> are described. This defines that the contents of the HTML file 381 obtained from the television receiver 21, which is designated by "TV.html", is described in the upper frame defined by the <FRAMESET> tag, and that the contents of the HTML file 382 obtained from the personal computer 31, which is designated by "PC.html", is described in the lower frame.

For example, the HTML file is edited such that the operation panel of the device detected previously by search is displayed on the upper frame. FIG. 32 is taken to be the case where the television receiver 21 is detected prior to the personal computer 31.

Figure 33:
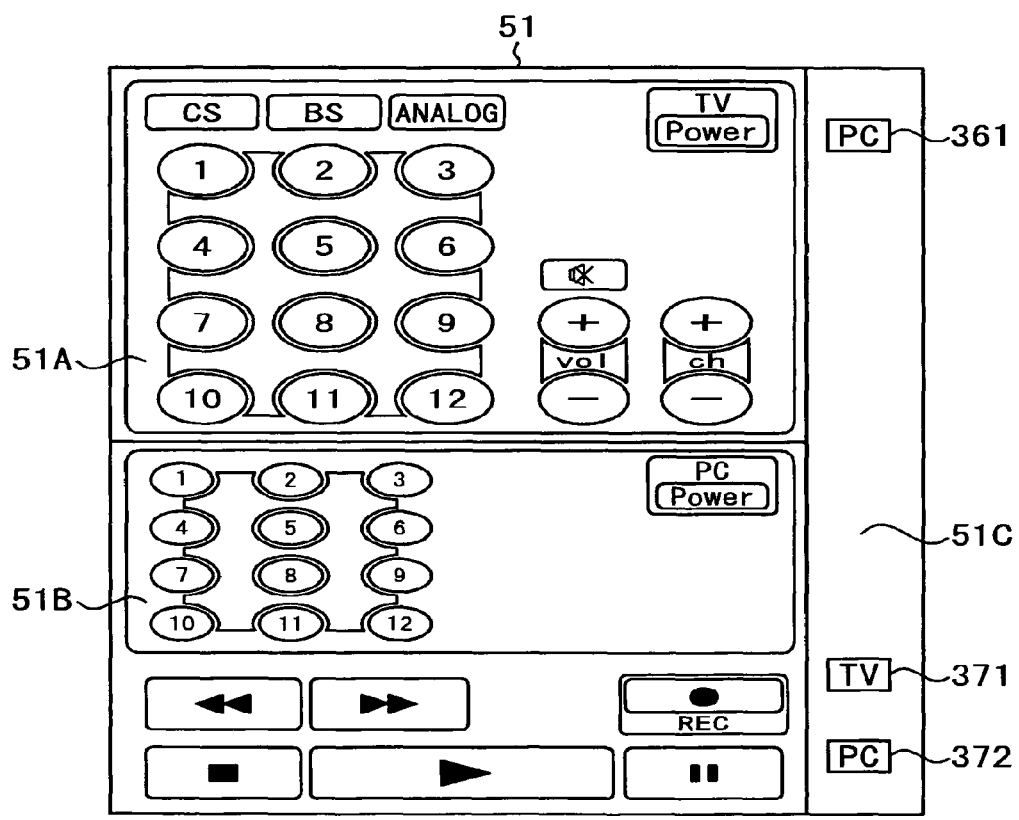
FIG. 33 is a diagram showing an example of display of an operation panel.

Based on the HTML file 383 to specify the above-mentioned frame split, in step S212, for example, the operation panels of FIG. 33 are displayed on the LCD 51.

As shown in FIG. 33, based on the HTML file 383 of FIG. 32, the operation panel of the television receiver 21 is displayed on a region (a frame) 51A formed on the upper half of the LCD 51, and the operation panel of the personal computer 31 is displayed on a region 51B formed on the lower half.

In this example, the operation panel to be operated when reproducing contents stored in the personal computer 351, or when causing the personal computer 351 to store predetermined contents, is shown as the operation panel of the personal computer 351.

A region 51C is formed at the right end of the LCD 51 in FIG. 33. An icon 361 to be operated when instructing it to display the operation panel of the personal computer 351 is displayed on the upper part of the region 51C. An icon 371 to be operated when instructing it to display the operation panel of the television receiver 21 that can communicate indirectly, and an icon 372 to be operated when instructing it to display the operation panel of the personal computer 31, are displayed on the lower part of the region 51C.

Image information of this icon is also to be provided from the device, together with the operation panel information.

As discussed above, even the operation panel of the devices that cannot communicate directly with the remote controller 1 is displayed in the similar manner as the operation panel of the device that can communicate directly. Therefore, without worrying whether or not direct communication is possible between the remote controller 1 and devices, a user can operate the devices.

The purpose of the user operation for connecting devices by the wireless LAN or the like is to have the devices link and perform a predetermined process, such as data sending/receiving. It can be said that the devices to be connected are devices having relevance with each other. Accordingly, by displaying not only the operation panel of a device located near the remote controller 1, but also the operation panel of a device connected via a network to the former device, a user can perform more efficiently predetermined process in which a plurality of devices are linked for execution with use of the remote controller 1.

Figure 34:
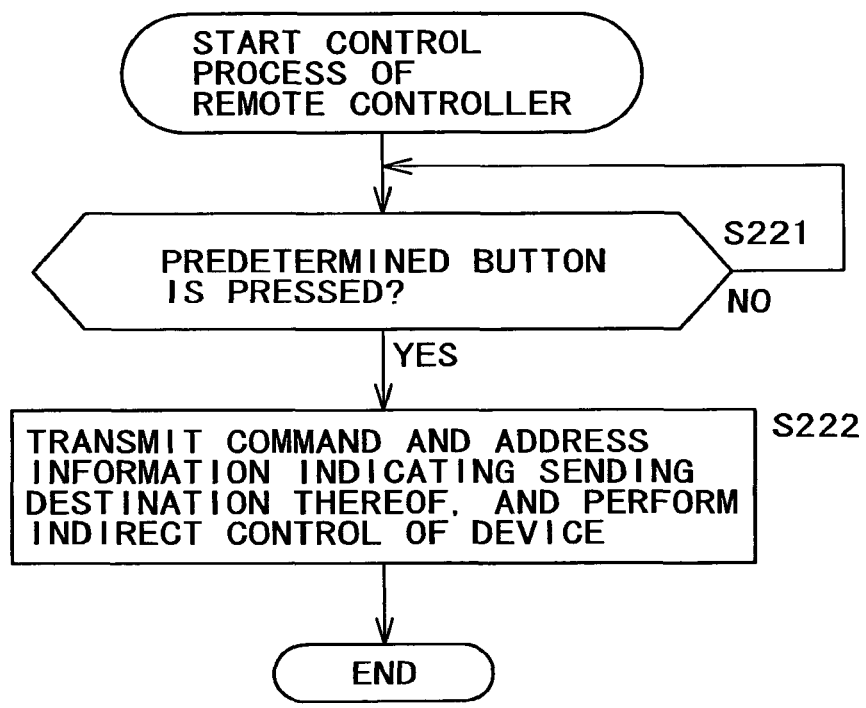
FIG. 34 is a flow chart for explaining a process of a remote controller that controls a device.

Referring to the flow chart of FIG. 34, a description will next be made of the process of the remote controller 1, in order to control a device indirectly via the device A.

For example, in the state in which the operation panel of FIG. 33 is displayed, the input detection section 154 determines in step S221 whether a predetermined button is pressed or not, which is disposed on the operation panel of the television receiver 21 (the upper part), or the operation panel of the personal computer 31 (the lower part), and waits until it determines that the button is pressed.

If the input detection section 154 determines in step S221 that a user presses the predetermined button, the process advances to step S222.

In step 222, the device control section 162 creates a command in response to the button pressed by the user, and sends the personal computer 351 (the device A) the created command and address information indicating the destination of the command, thereby controlling indirectly the television receiver 21 or the personal computer 31.

The television receiver 21 or the personal computer 31, which has received the command, performs an operation in accordance with the command.

In the foregoing, the indirectly controllable device is taken to be a so-called "child" device, which is connected via a network to the device that can communicate directly with the remote controller 1. Alternatively, it may be configured such that the remote controller 1 may also operate a "grandchild" device, which is connected via another network to the "child" device.

In other words, the "child" device is connected to two networks (the network on which the "parent" device is present, and the network on which the "grandchild" device is present).

Even in this case, by the similar process as described above, device information and operation panel information, or information such as various messages are sent/received between the remote controller 1 and the "grandchild" device, by way of the "child" device and the "parent device."

Additionally, in the foregoing, the device information of the television receiver 21 and the personal computer 31 are obtained from the respective devices by way of the personal computer 351. Alternatively, their respective device information may previously be obtained by the personal computer 351, so as to be provided from the personal computer 351 to the remote controller 1.

Referring to the flow chart of FIG. 35, a description will be made of the process in the case where the device A manages the device information of the device B and the device C, and provided it to the remote controller 1. That is, the process of FIG. 35 corresponds to the process of FIG. 22 and FIG. 23.

The processes in step S231 to S233, and steps S241 and S242 are the similar to the process in step S101 to S103 in FIG. 22, and steps S121 and S122, respectively. Specifically, the remote controller 1 requests the device A detected by search, to send device information in step S231, and receives the device information of the device A sent in response to the request in step S232. The received device information of the device A is registered in step S233.

In step S234, the remote controller 1 inquires of the device A information of devices that can be controlled indirectly by interposing the device A.

The device A has obtained the information of the device B and the device C from the device B and the device C, respectively, for example, when connection by wireless LAN is established.

The inquiry from the remote controller 1 is received by the device A in step S243.

In step S234, the device A sends the remote controller 1 the respective device information of the device B and the device C. The sent device information is received in step S235, and the process advances to step S236 to register it.

As discussed above, the respective device information of the device B and the device C are provided from the device A to the remote controller 1. As apparent from the comparison with FIG. 22 and FIG. 23, it is possible to omit the process for device information requests and for device information transmission, which are performed separately from the remote controller 1 to the respective devices.

In a similar manner, the operation panel information and the like of the device B and the device C may be acquired previously by the device A, so as to be provided to the remote controller 1.

Although the foregoing description has mainly been made of the case where communication is performed between the remote controller 1 and the devices by Bluetooth communication, it is also possible to similarly use a variety of wireless communication such as IEEE802.11a and IEEE802.11b.

Although in the foregoing, the devices to be controlled by the remote controller 1 are the television receiver 21, the audio system 22, the personal computer 31 and the robot 32 in FIG. 1, it is also capable of configuring such that various equipment other than these are controlled by the remote controller 1. For example, the remote controller 1 may control audio visual (AV) equipment such as DVD recorders and hard disk recorders, appliances such as illumination equipment and air conditioners, and other equipment. Even in this case, respective equipment store information of the operation panel to be operated when controlling the equipment, and the stored operation panel information are provided to the remote controller 1.

Although the foregoing description has mainly be made of the case where the personal computer 351 is connected to the television receiver 21 and the personal computer 31 by the wireless LAN in accordance with IEEE802.11b, it is also possible to use, as a network, various wireless communication such as IEEE802.11a, or various wire communication such as Ethernet (registered trademark).

Although the foregoing sequence of process is executable by hardware, it is also executable by software.

In the case of having a software execute the sequence of processes, a program constituting the software is installed from a network or a recording medium on a computer incorporated into a dedicated hardware, or, for example, on a general-purpose personal computer capable of executing a variety of functions by installing various programs.

This recording medium is constituted not only by package media distributed so as to provide a program for the user independently of a device itself, as shown in FIG. 3, which comprised of the magnetic disk 71 (including a flexible disk), the optical disk 72 (including a compact disk-read only memory (CD-ROM)), and a digital versatile disk (DVD)), the magneto-optical disk 73 (including an mini-disk (MD (registered trademark))), or the semiconductor memory 74, on which a program is recorded, but also by the ROM 62 on which a program is recorded or a hard disk contained in the storage section 69, which is already incorporated into a device itself so as to be provided for the user.

In the present specification, the steps of describing a program to be recorded in a recording medium includes, of course, the process performed in time series in a described sequence, as well as the process executed in parallel or individually, even if it is not necessarily executed in time series.

Moreover, in the present specification, the system denotes the entire apparatus composed of a plurality of devices.

INDUSTRIAL APPLICABILITY

In accordance with the present invention, it is capable of controlling an information processing apparatus existing in the vicinity.

Moreover, in accordance with the present invention, it is possible to control not only information processing apparatuses existing in the vicinity, but also an information processing apparatus connected via a network to the former information processing apparatus.

Furthermore, in accordance with the present invention, it is possible to control information processing apparatuses more efficiently and quickly.

The invention claimed is:
1. A control apparatus comprising:
a display; and
a processing circuitry configured to:
store at least one first operation panel information corresponding to at least one first device received from a second device;
detect the at least one first device when at least a portion of the control apparatus is picked up by a user;
determine whether the at least one first operation panel information remains stored in the control apparatus;
display at least one first operation panel on the display based on the at least one first operation panel information if the at least one first operation panel information remains stored in the control apparatus; and
control the at least one first device.

2. The control apparatus according to claim 1, wherein the processing circuitry is further configured to request the at least one first operation panel information from the second device.

3. The control apparatus according to claim 1, wherein the processing circuitry is further configured to receive device information from the at least one first device detected by the control apparatus and to register the device information.

4. The control apparatus according to claim 3, wherein the processing circuitry is further configured to register address information of the at least one first device detected.

5. The control apparatus according to claim 3, wherein the processing circuitry is further configured to receive information regarding another device from the at least one first device.

6. The control apparatus according to claim 3, wherein the device information comprises device identification information.

7. The control apparatus according to claim 2, wherein the second device sends the at least one first operation panel information according to a hardware configuration of the control apparatus.

8. The control apparatus according to claim 1, wherein the processing circuitry is further configured to edit the at least one first operation panel information and to display the at least one first operation panel based on the edited at least one first operation panel information.

9. A processor-implemented control method comprising:
storing, via a control apparatus, at least one first operation panel information corresponding to at least one first device received from a second device;
detecting, via the control apparatus, the at least one first device when at least a portion of the control apparatus is picked up by a user;
determining, via the control apparatus, whether the at least one first operation panel information remains stored in the control apparatus;

displaying, on a display coupled to the control apparatus, at least one first operation panel based on the at least one first operation panel information if the at least one first operation panel information remains stored in the control apparatus; and controlling the at least one first device.

10. The processor-implemented control method according to claim 9, further comprising requesting, via the control apparatus, the at least one first operation panel information from the second device.

11. The processor-implemented control method according to claim 9, further comprising receiving, via the control apparatus, device information from the at least one first device detected by the control apparatus and registering, via the control apparatus, the device information.

12. The processor-implemented control method according to claim 11, further comprising registering, via the control apparatus, address information of the at least one first device detected.

13. The processor-implemented control method according to claim 11, further comprising receiving, via the control apparatus, information regarding another device from the at least one first device.

14. The processor-implemented control method according to claim 11, wherein the device information comprises device identification information.

15. The processor-implemented control method according to claim 10, wherein the second device sends the at least one first operation panal information according to a hardware configuration of the control apparatus.

16. The processor-implemented control method according to claim 9, further comprising editing, via the control apparatus, the at least one first operation panel information and displaying, via the control apparatus, the at least one first operation panel based on the edited at least one first operation panel information.

17. A non-transitory computer-readable recording medium storing instructions that are executable by one or more processors to cause the one or more processors to perform a method for controlling at least one first device, the method comprising:

storing, via a control apparatus, at least one first operation panel information corresponding to at least one first device received from a second device;

detecting, via the control apparatus, the at least one first device when at least a portion of the control apparatus is picked up by a user;

determining, via the control apparatus, whether the at least one first operation panel information remains stored in the control apparatus;

displaying, on a display coupled to the control apparatus, at least one first operation panel based on the at least one first operation panel information if the at least one first operation panel information remains stored in the control apparatus; and controlling the at least one first device.

18. The non-transitory computer-readable medium according to claim 17, further comprising requesting, via the control apparatus, the at least one first operation panel information from the second device.

19. The non-transitory computer-readable medium according to claim 17, further comprising receiving, via the control apparatus, device information from the at least one first device detected by the control apparatus and registering, via the control apparatus, the device information.

20. The non-transitory computer-readable medium according to claim 19, further comprising registering, via the control apparatus, address information of the at least one first device detected.

21. The non-transitory computer-readable medium according to claim 19, further comprising receiving, via the control apparatus, information regarding another device from the at least one first device.

22. The non-transitory computer-readable medium according to claim 19, wherein the device information comprises device identification information.

23. The non-transitory computer-readable medium according to claim 18, wherein the second device sends the at least one first operation panal information according to a hardware configuration of the control apparatus.

24. The non-transitory computer-readable medium according to claim 17, further comprising editing, via the control apparatus, the at least one first operation panel information and displaying, via the control apparatus, the at least one first operation panel based on the edited at least one first operation panel information.

* * * * *